(12) United States Patent
Simmons et al.

(10) Patent No.: US 9,908,093 B2
(45) Date of Patent: Mar. 6, 2018

(54) PROCESS FOR CONVERTING A CARBONACEOUS MATERIAL TO METHANE, METHANOL AND/OR DIMETHYL ETHER USING MICROCHANNEL PROCESS TECHNOLOGY

(75) Inventors: Wayne W. Simmons, Dublin, OH (US); Robert Dwayne Litt, Westerville, OH (US); Terry Mazanec, Solon, OH (US); Anna Lee Tonkovich, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 0 days.

(21) Appl. No.: 12/420,942

(22) Filed: Apr. 9, 2009

(65) Prior Publication Data
US 2009/0259076 A1 Oct. 15, 2009

Related U.S. Application Data

(60) Provisional application No. 61/043,470, filed on Apr. 9, 2008.

(51) Int. Cl.
| | | |
|---|---|---|
| *B01J 19/00* | (2006.01) | |
| *C01B 3/22* | (2006.01) | |
| *C01B 3/32* | (2006.01) | |
| *C01B 3/50* | (2006.01) | |
| *C01B 3/52* | (2006.01) | |
| *C01B 3/56* | (2006.01) | |
| *C07C 1/04* | (2006.01) | |
| *C07C 1/20* | (2006.01) | |
| *C07C 2/84* | (2006.01) | |
| *C07C 9/06* | (2006.01) | |
| *C07C 11/04* | (2006.01) | |
| *C07C 29/152* | (2006.01) | |
| *C10J 3/00* | (2006.01) | |

(52) U.S. Cl.
CPC ............. *B01J 19/0093* (2013.01); *C01B 3/22* (2013.01); *C01B 3/32* (2013.01); *C01B 3/501* (2013.01); *C01B 3/52* (2013.01); *C01B 3/56* (2013.01); *C07C 1/04* (2013.01); *C07C 1/20* (2013.01); *C07C 2/84* (2013.01); *C07C 9/06* (2013.01); *C07C 11/04* (2013.01); *C07C 29/152* (2013.01); *C10J 3/00* (2013.01); *B01J 2219/0086* (2013.01); *B01J 2219/00835* (2013.01); *B01J 2219/00846* (2013.01); *B01J 2219/00873* (2013.01); *B01J 2219/00918* (2013.01); *B01J 2219/00921* (2013.01); *B01J 2219/00984* (2013.01); *C01B 2203/0205* (2013.01); *C01B 2203/0266* (2013.01); *C01B 2203/042* (2013.01); *C01B 2203/043* (2013.01); *C01B 2203/0405* (2013.01); *C01B 2203/0415* (2013.01); *C01B 2203/0465* (2013.01); *C01B 2203/0475* (2013.01); *C01B 2203/0485* (2013.01); *C01B 2203/06* (2013.01); *C01B 2203/061* (2013.01); *C01B 2203/062* (2013.01); *C01B 2203/0838* (2013.01); *C01B 2203/0883* (2013.01); *C01B 2203/1217* (2013.01); *C01B 2203/84* (2013.01); *C07C 2529/85* (2013.01); *C10J 2300/1662* (2013.01); *C10J 2300/1665* (2013.01); *Y02E 50/18* (2013.01); *Y02E 50/32* (2013.01); *Y02E 50/346* (2013.01); *Y02P 30/42* (2015.11)

(58) Field of Classification Search
USPC .................................. 568/671, 840; 585/310
See application file for complete search history.

(56) References Cited

U.S. PATENT DOCUMENTS

| | | | |
|---|---|---|---|
| 3,882,049 A | 5/1975 | Bertolacini et al. | |
| 3,972,837 A | 8/1976 | Acres et al. | |
| 4,017,272 A * | 4/1977 | Anwer et al. ............... | 48/197 R |
| 4,089,810 A | 5/1978 | Diwell et al. | |
| 4,096,095 A | 6/1978 | Cairns | |
| 4,110,359 A | 8/1978 | Marion | |
| 4,122,110 A | 10/1978 | Sugier et al. ............... | 260/449.5 |
| 4,130,575 A | 12/1978 | Jorn .............................. | 260/449 |
| 4,289,652 A | 9/1981 | Hunter et al. | |
| 4,298,354 A | 11/1981 | Hardman et al. ................. | 44/56 |
| 4,342,643 A | 8/1982 | Kyan ............................ | 208/134 |
| 4,348,487 A | 9/1982 | Goldstein et al. ............ | 518/704 |
| 4,423,272 A | 12/1983 | Forbus et al. ................ | 585/640 |
| 4,492,773 A | 1/1985 | Ball et al. ...................... | 518/713 |
| 4,525,482 A | 6/1985 | Ohsaki et al. ................. | 518/707 |

(Continued)

FOREIGN PATENT DOCUMENTS

| | | |
|---|---|---|
| DE | 246257 | 6/1987 |
| DE | 3926466 | 2/1991 |
| EP | 1 434 652 B1 | 2/2005 |
| EP | 1 248 675 B1 | 8/2005 |
| EP | 1 559 475 B1 | 8/2005 |
| EP | 1 567 616 B1 | 8/2006 |
| EP | 1102628 | 11/2006 |
| GB | 1531134 | 11/1978 |
| GB | 2077136 | 12/1981 |

(Continued)

OTHER PUBLICATIONS

Chinese Office Action, Application No. 200980121451.8, issued Jan. 16, 2013.

(Continued)

*Primary Examiner* — Rosalynd A Keys
(74) *Attorney, Agent, or Firm* — Renner, Otto, Boisselle & Sklar, LLP

(57) ABSTRACT

This invention relates to a process for converting a carbonaceous material to a desired product comprising methane, methanol and/or dimethyl ether, the process comprising: gasifying the carbonaceous material at a temperature in excess of about 700° C. to form synthesis gas; and flowing the synthesis gas through two or more reaction zones in a microchannel reactor to convert the synthesis gas to the desired product.

59 Claims, 10 Drawing Sheets

(56) References Cited

U.S. PATENT DOCUMENTS

| | | | |
|---|---|---|---|
| 4,540,714 A | 9/1985 | Pedersen et al. | 518/714 |
| 4,588,560 A | 5/1986 | Degnan et al. | 422/211 |
| 4,596,782 A | 6/1986 | Courty et al. | |
| 4,675,344 A | 6/1987 | Conway et al. | 518/714 |
| 4,752,622 A | 6/1988 | Stevens | 518/714 |
| 4,752,623 A | 6/1988 | Stevens et al. | 518/714 |
| 4,762,858 A | 8/1988 | Hucul et al. | 518/714 |
| 4,795,841 A | 1/1989 | Elliott et al. | 585/240 |
| 4,843,101 A | 6/1989 | Klier et al. | 518/713 |
| 5,180,868 A | 1/1993 | Baker et al. | 585/240 |
| 5,248,251 A | 9/1993 | Dalla Betta et al. | |
| 5,492,617 A | 2/1996 | Trimble et al. | 208/148 |
| 5,525,311 A | 6/1996 | Girod et al. | 422/200 |
| 5,538,700 A | 7/1996 | Koves | 422/200 |
| 5,540,899 A | 7/1996 | Koves | 422/200 |
| 5,600,053 A | 2/1997 | Girod et al. | 585/654 |
| 5,660,715 A | 8/1997 | Trimble et al. | 208/148 |
| 5,703,133 A | 12/1997 | Vanderspurt et al. | 518/707 |
| 5,948,240 A | 9/1999 | Mulvaney, III et al. | 208/79 |
| 6,040,266 A | 3/2000 | Fay, III et al. | |
| 6,159,358 A | 12/2000 | Mulvaney, III et al. | 208/46 |
| 6,248,796 B1 | 6/2001 | Jackson et al. | 518/714 |
| 6,274,101 B1 | 8/2001 | Sechrist | 422/198 |
| 6,312,586 B1 | 11/2001 | Kalnes et al. | 208/80 |
| 6,326,326 B1 | 12/2001 | Feng et al. | 502/62 |
| 6,334,994 B1 | 1/2002 | Wendelbo et al. | 423/718 |
| 6,409,072 B1 | 6/2002 | Breuer et al. | 228/111.5 |
| 6,432,369 B1 | 8/2002 | Mulvaney, III et al. | 422/213 |
| 6,440,895 B1 | 8/2002 | Tonkovich et al. | |
| 6,488,838 B1 | 12/2002 | Tonkovich et al. | 208/108 |
| 6,531,224 B1 | 3/2003 | Fryxell et al. | 428/405 |
| 6,534,677 B1 | 3/2003 | White et al. | 562/486 |
| 6,555,725 B1 | 4/2003 | Wittenbrink et al. | 585/734 |
| 6,570,047 B1 | 5/2003 | Mart et al. | 585/899 |
| 6,579,343 B2 | 6/2003 | Brennecke et al. | 95/51 |
| 6,620,398 B2 | 9/2003 | Kindig et al. | 423/359 |
| 6,663,681 B2 | 12/2003 | Kindig et al. | 48/127.5 |
| 6,682,714 B2 | 1/2004 | Kindig et al. | 423/657 |
| 6,685,754 B2 | 2/2004 | Kindig et al. | 48/210 |
| 6,703,429 B2 | 3/2004 | O'Rear et al. | 518/706 |
| 6,713,036 B1 | 3/2004 | Vanden Bussche | 423/584 |
| 6,733,835 B2 | 5/2004 | Fryxell et al. | 427/299 |
| 6,743,962 B2 | 6/2004 | O'Rear et al. | 585/717 |
| 6,753,038 B2 | 6/2004 | Fryxell et al. | 427/337 |
| 6,768,035 B2 | 7/2004 | O'Rear et al. | 585/331 |
| 6,846,554 B2 | 1/2005 | Fryxell et al. | 428/307.3 |
| 6,969,506 B2 | 11/2005 | Tonkovich et al. | 423/652 |
| 7,012,104 B2 | 3/2006 | Espinoza et al. | 518/715 |
| 7,019,038 B2 | 3/2006 | Espinoza et al. | 518/700 |
| 7,045,114 B2 | 5/2006 | Tonkovich et al. | 423/659 |
| 7,067,560 B2 | 6/2006 | Bowe | 518/700 |
| 7,067,561 B2 | 6/2006 | Bowe | 518/706 |
| 7,071,239 B2 | 7/2006 | Ortego, Jr. et al. | 518/715 |
| 7,084,180 B2 | 8/2006 | Wang et al. | 518/712 |
| 7,087,651 B2 | 8/2006 | Lee-Tuffnell et al. | 518/700 |
| 7,108,070 B2 | 9/2006 | Hall et al. | 166/357 |
| 7,109,248 B2 | 9/2006 | Bowe | 518/700 |
| 7,122,106 B2 | 10/2006 | Lin et al. | 205/109 |
| 7,183,329 B2 | 2/2007 | Green et al. | 518/715 |
| 7,232,472 B2 | 6/2007 | Kindig et al. | 48/127.5 |
| 7,294,734 B2 | 11/2007 | Brophy et al. | 558/317 |
| 7,304,012 B2 | 12/2007 | Green et al. | 502/180 |
| 2002/0028164 A1 | 3/2002 | Schutte et al. | 422/198 |
| 2002/0192099 A1 | 12/2002 | Zech et al. | 422/99 |
| 2003/0007904 A1 | 1/2003 | Tonkovich et al. | 422/180 |
| 2003/0225169 A1 | 12/2003 | Yetman | 518/726 |
| 2004/0034111 A1 | 2/2004 | Tonkovich et al. | 518/726 |
| 2004/0134660 A1 | 7/2004 | Hall et al. | 166/357 |
| 2004/0180971 A1 | 9/2004 | Inoue et al. | |
| 2004/0188326 A1 | 9/2004 | Tonkovich et al. | 208/139 |
| 2004/0229752 A1 | 11/2004 | Long et al. | 502/303 |
| 2005/0163701 A1 | 7/2005 | Tonkovich et al. | 423/584 |
| 2005/0165121 A1 | 7/2005 | Wang et al. | 518/726 |
| 2005/0176832 A1 | 8/2005 | Tonkovich et al. | 518/726 |
| 2005/0282918 A1 | 12/2005 | Bowe | 518/726 |
| 2006/0020155 A1 | 1/2006 | Beech, Jr. et al. | 585/639 |
| 2006/0036106 A1 | 2/2006 | Mazanec et al. | 549/533 |
| 2006/0041029 A1 | 2/2006 | Bowe et al. | 518/700 |
| 2006/0074134 A1 | 4/2006 | O'Rear et al. | 518/726 |
| 2006/0135630 A1 | 6/2006 | Bowe | 518/702 |
| 2006/0142400 A1 | 6/2006 | Bowe | 518/703 |
| 2006/0251552 A1 | 11/2006 | Wang et al. | 422/190 |
| 2006/0251558 A1 | 11/2006 | Chinn et al. | 423/230 |
| 2007/0004810 A1 | 1/2007 | Wang et al. | 518/718 |
| 2007/0078285 A1 | 4/2007 | Dagle et al. | |
| 2007/0197801 A1 | 8/2007 | Bolk et al. | 549/229 |
| 2007/0197808 A1 | 8/2007 | Bolk et al. | 549/536 |
| 2007/0244000 A1 | 10/2007 | Molinier et al. | 502/300 |
| 2008/0058434 A1 | 3/2008 | Tonkovich et al. | |
| 2008/0081844 A1 | 4/2008 | Shires et al. | |
| 2008/0103220 A1* | 5/2008 | Cherry et al. | 518/702 |

FOREIGN PATENT DOCUMENTS

| | | |
|---|---|---|
| RU | 2047650 C1 * | 11/1995 |
| WO | 9421372 | 9/1994 |
| WO | 9700442 | 1/1997 |
| WO | 9828073 | 7/1998 |
| WO | 9838147 | 9/1998 |
| WO | 9916542 | 4/1999 |
| WO | 0006301 | 2/2000 |
| WO | 01/93976 | 12/2001 |
| WO | 02/34863 | 5/2002 |
| WO | 02/064248 | 8/2002 |
| WO | 03006149 | 1/2003 |
| WO | 03/049835 | 6/2003 |
| WO | 03/048035 | 12/2003 |
| WO | 03/106386 | 12/2003 |
| WO | 2004/037418 | 5/2004 |
| WO | 2004/091771 | 10/2004 |
| WO | 2004/096952 | 11/2004 |
| WO | 2005/003025 | 1/2005 |
| WO | 2005/003632 | 1/2005 |
| WO | 2005/090521 | 9/2005 |
| WO | 2005/090522 | 9/2005 |
| WO | 2005082519 | 9/2005 |
| WO | 2005/102511 | 11/2005 |
| WO | 2005/123883 | 12/2005 |
| WO | 2006/033025 | 3/2006 |
| WO | 2006/043111 | 4/2006 |
| WO | 2006/075130 | 7/2006 |
| WO | 2006/075193 | 7/2006 |
| WO | 2006/079848 | 8/2006 |
| WO | 2006/090189 | 8/2006 |
| WO | 2006/095204 | 9/2006 |
| WO | 2006102675 | 9/2006 |
| WO | 2006/127889 | 11/2006 |
| WO | 2007/008495 | 1/2007 |
| WO | 2007/027767 | 3/2007 |
| WO | 2007/071737 | 6/2007 |
| WO | 2007/071741 | 6/2007 |
| WO | 2007/071744 | 6/2007 |
| WO | 2007/076393 | 7/2007 |
| WO | 2007/076394 | 7/2007 |
| WO | 2007/076395 | 7/2007 |
| WO | 2007/076397 | 7/2007 |
| WO | 2007/076400 | 7/2007 |
| WO | 2007/076402 | 7/2007 |
| WO | 2007/076404 | 7/2007 |
| WO | 2007/076406 | 7/2007 |
| WO | 2008/030467 | 3/2008 |
| WO | 2008/104793 | 9/2008 |
| ZA | 855317 | 7/1985 |

OTHER PUBLICATIONS

International Search Report and Written Opinion, Application No. PCT/US2009/039994, mailed Dec. 17, 2009.

"Smaller Scale GTL Plants Solve Associated Gas, Remote Location Problems"; *Syngas Refiner*, Dec. 1, 2006; pp. 15, 17.

Miller et al.; "Selection of a Hydrogen Separation Process"; presented at the 1989 NPRA Annual Meeting held Mar. 19-21, San Francisco; pp. 1-27.

(56) References Cited

OTHER PUBLICATIONS

Subramani et al.; "A Review of Recent Literature to Search for an Efficient Catalytic Process for the Conversion of Syngas to Ethanol"; *Energy & Fuels,* vol. xxx, No. xx, XXX. Published on Web Jan. 31, 2008.

Elliott; "Historical Developments in Hydroprocessing Bio-oils"; *Energy & Fuels,* 2007, 21, pp. 1792-1815.

Green Car Congress, Energy, Technologies, Issues and Policies for Sustainable Mobility, www.greencarcongress.com, Jan. 16, 2008, 7 pages.

Kandlikar; Exploring Roughness Effect on Laminar Internal Flow—Are We Ready for Change?; *Nanoscale and Microscale Thermophysical Engineering,* 12; 2008; pp. 61-82.

Technology Review: Fuel from Waste; Technology Review published by MIT; Dec. 21, 2007; www.technologyreview.com/Energy/19974, 5 pages.

U.S. Department of Energy, Energy Efficiency and Renewable Energy, Biomass Program; "Pyrolysis and Other Thermal Processing"; www.eere.energy.gov/biomass/pyrolysis.html; content last updated Oct. 13, 2005, 3 pages.

Holmen; Direct conversion of methane to fuels and chemicals;; *Catalysis Today,* 142 (2009); pp. 2-8.

Chen et al.; "Performance analysis of a folding flow micromixer"; Microfluid Nanofluid (2009) 6:763-774.

MacInnes et al.; "Investigation of alternating-flow mixing in microchannels"; Chemical Engineering Science 60; 2005; pp. 3453-3467.

MacInnes et al.; "Numerial characterization of floding flow microchannel mixers"; Chemical Engineering Science 62; 2007; pp. 2718-2727.

MacInnes et al.; "Mixing Strategies for Flow in Microchannel Devices"; Chemical and Process Engineering, University of Sheffield, Nov. 24, 2004.

Cybulski et al.; "Monoliths in Heterogeneous Catalysis"; Catal. Rev.—Sci. Eng., 36(2), 179-270 (1994).

Bennett et al.; "Microchannel cooled heatsinks for high average power laser diode arrays"; SPIE, vol. 1865; 1993; pp. 144-153.

Iglesia; "Design, synthesis, and use of cobalt-based Fischer-Tropsch synthesis catalysts"; Applied Catalysis A: General 161 (1997); pp. 59-78.

International Preliminary Report on Patentability, Application No. PCT/US2009/039994, dated Oct. 21, 2010.

Chinese Office Action, Application No. 200980121451.8, dated Oct. 12, 2013.

Chinese Office Action, Application No. 200980121451.8, dated May 5, 2014.

European Office Action, Application No. 09 729 481.3, dated Aug. 4, 2014.

Australian Office Action, Application No. 2009233786, dated Jun. 13, 2013.

Horgan et al.; Integrated Home Energy from Waste & Biomass; Berkshire Energy Laboratory, LLC; Feb. 6, 2009.

Chemical Engineering; "Compact Reactors Boost Productivity"; Oct. 1, 2011; pp. 1/4-4-4.

* cited by examiner

PROCESS FOR CONVERTING A CARBONACEOUS MATERIAL TO METHANE, METHANOL AND/OR DIMETHYL ETHER USING MICROCHANNEL PROCESS TECHNOLOGY

This application claims priority under 35 U.S.C. § 119(e) to U.S. Provisional Application Ser. No. 61/043,470, filed Apr. 9, 2008. This prior application is incorporated herein by reference.

TECHNICAL FIELD

This invention relates to a process for converting a carbonaceous material (e.g., biomass, solid waste, etc.) to methane, methanol and/or dimethyl ether (DME) using microchannel process technology.

BACKGROUND

Methane, methanol and dimethyl ether are chemicals that have numerous uses.

SUMMARY

A problem with providing these chemicals relates to providing raw materials for their production that are plentiful and relatively inexpensive. This invention provides a solution to this problem. The present invention relates to a process for converting carbonaceous materials such as biomass, solid-waste, and the like, to a product comprising methane, methanol and/or dimethyl ether. The process involves converting the carbonaceous material to synthesis gas, and then converting the synthesis gas to methane, methanol and/or dimethyl ether using a microchannel reactor. The microchannel reactor may be relatively compact and readily transportable. As such, the inventive process may be adapted for use at locations that are at or near the source of the raw materials. For example, with the inventive process it is may be possible to convert waste products (e.g., trash, garbage, and the like) into methane, methanol and/or dimethyl ether on a relatively small scale of about 50 to about 500 cubic meters of gas or liters of liquid per day. The inventive process may also be adapted for use with larger scale operations. For example, carbonaceous materials such as municipal solid waste may be converted to methane, methanol and/or dimethyl ether on a scale of thousands or tens of thousands of cubic meters of gas or liters of liquid per day.

This invention relates to a process for converting a carbonaceous material to a desired product comprising methane, methanol and/or dimethyl ether, the process comprising: (A) gasifying the carbonaceous material at a temperature of at least about 700° C. to form synthesis gas; (B)(I) flowing the synthesis gas through a first reaction zone in a microchannel reactor at a first reaction temperature in contact with a first catalyst to form an intermediate product composition, the intermediate product composition comprising synthesis gas and the desired product, the approach to equilibrium for conversion of the synthesis gas in the first reaction zone being at least about 5%, and exchanging heat between the first reaction zone and a heat exchanger; and (B)(II) flowing the intermediate product composition from the previous step through another reaction zone in the microchannel reactor at another reaction temperature in contact with another catalyst to form the desired product, the approach to equilibrium for conversion of the synthesis gas in the another reaction zone being at least about 5%; and exchanging heat between the another reaction zone and the heat exchanger.

BRIEF DESCRIPTION OF THE DRAWINGS

In the annexed drawings like parts and features have like references. A number of the drawings are schematic illustrations which may not necessarily be drawn to scale.

In FIGS. 8 and 9, five microchannel reactors are shown.

FIGS. 17-19 are schematic illustrations of fin assemblies that may be used for supporting the catalyst.

DETAILED DESCRIPTION

Figure 1:
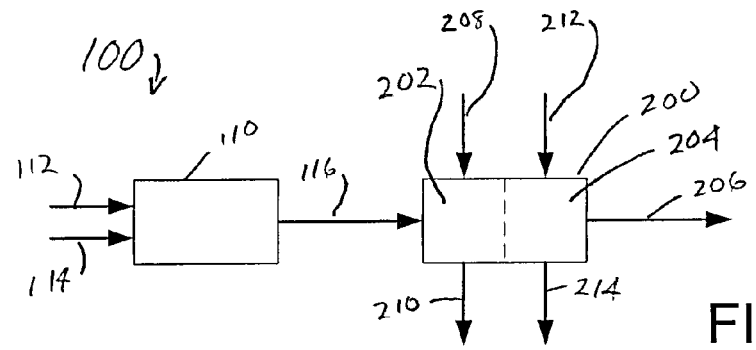
FIG. 1 is a flow sheet illustrating the inventive process in a particular form, the process comprising converting a carbonaceous material into methane, methanol and/or dimethyl ether using a gasifier in combination with a microchannel reactor. The carbonaceous material is converted to synthesis gas in the gasifier. The synthesis gas is converted to methane, methanol and/or dimethyl ether in the microchannel reactor. The microchannel reactor includes one or more process microchannels. Each process microchannel contains a first reaction zone and a second or another reaction zone downstream of the first reaction zone. Heat exchange fluid flows through one or more heat exchange channels that are adjacent to and/or in thermal contact with the process microchannels. The heat exchange fluid flows in a direction that is cross-current relative to the flow of process fluid in the one or more process microchannels.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural. All combinations specified in the claims may be combined in any manner.

The term "microchannel" may refer to a channel having at least one internal dimension of height or width of up to about 10 millimeters (mm), and in one embodiment up to about 5 mm, and in one embodiment up to about 2 mm, and in one embodiment up to about 1 mm. The microchannel may comprise at least one inlet and at least one outlet wherein the at least one inlet is distinct from the at least one outlet. The microchannel may not be merely an orifice. The microchannel may not be merely a channel through a zeolite or a mesoporous material. The length of the microchannel may be at least about two times the height or width, and in one embodiment at least about five times the height or width, and in one embodiment at least about ten times the height or width. The internal height or width of the microchannel may be in the range of about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other internal dimension of height or width may be of any dimension, for example, up to about 3 meters, and in one embodiment about 0.01 to about 3 meters, and in one embodiment about 0.1 to about 3 meters. The length of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. The microchannel may have a cross section having any shape, for example, a square, rectangle, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "microchannel reactor" may refer to an apparatus comprising one or more process microchannels wherein a reaction process is conducted. The process may comprise a process for converting synthesis gas to methane, methanol and/or dimethyl ether. When two or more process microchannels are used, the process microchannels may be operated in parallel. The microchannel reactor may include a header or manifold assembly for providing for the flow of fluid into the one or more process microchannels, and a footer or manifold assembly providing for the flow of fluid out of the one or more process microchannels. The microchannel reactor may comprise one or more heat exchange channels adjacent to and/or in thermal contact with the one or more process microchannels. The heat exchange channels may provide cooling for the fluids in the process microchannels. The heat exchange channels may be microchannels. The microchannel reactor may include a header or manifold assembly for providing for the flow of heat exchange fluid into the heat exchange channels, and a footer or manifold assembly providing for the flow of heat exchange fluid out of the heat exchange channels.

The term "process microchannel" may refer to a microchannel wherein a process is conducted. The process may comprise a process for converting synthesis gas to methane, methanol and/or dimethyl ether.

The term "volume" with respect to volume within a process microchannel may include all volume in the process microchannel a process fluid may flow through or flow by. This volume may include volume within surface features that may be positioned in the process microchannel and adapted for the flow of fluid in a flow-through manner or in a flow-by manner.

The term "adjacent" when referring to the position of one channel relative to the position of another channel may mean directly adjacent such that a wall or walls separate the two channels. In one embodiment, the two channels may have a common wall. The common wall may vary in thickness. However, "adjacent" channels may not be separated by an intervening channel that may interfere with heat transfer between the channels. One channel may be adjacent to another channel over only part of the dimension of the another channel. For example, a process microchannel may be longer than and extend beyond one or more adjacent heat exchange channels.

The term "thermal contact" may refer to two bodies, for example, two channels, that may or may not be in physical contact with each other or adjacent to each other but still exchange heat with each other. One body in thermal contact with another body may heat or cool the other body.

The term "fluid" may refer to a gas, a liquid, a mixture of a gas and a liquid, or a gas or a liquid containing dispersed solids, liquid droplets and/or gaseous bubbles. The droplets and/or bubbles may be irregularly or regularly shaped and may be of similar or different sizes.

The terms "gas" and "vapor" may have the same meaning and may be used interchangeably.

The term "residence time" or "average residence time" may refer to the internal volume of a space within a channel occupied by a fluid flowing in the space divided by the average volumetric flow rate for the fluid flowing in the space at the temperature and pressure being used.

The terms "upstream" and "downstream" may refer to positions within a channel (e.g., a process microchannel) or in a process flow sheet that is relative to the direction of flow of a fluid in the channel or process flow sheet. For example, a position within a channel or process flow sheet not yet reached by a portion of a fluid stream flowing toward that position would be downstream of that portion of the fluid stream. A position within the channel or process flow sheet already passed by a portion of a fluid stream flowing away from that position would be upstream of that portion of the fluid stream. The terms "upstream" and "downstream" do not necessarily refer to a vertical position since the channels used herein may be oriented horizontally, vertically or at an inclined angle.

The term "shim" may refer to a planar or substantially planar sheet or plate. The thickness of the shim may be the smallest dimension of the shim and may be up to about 4 mm, and in one embodiment in the range from about 0.05 to about 2 mm, and in one embodiment in the range of about 0.05 to about 1 mm, and in one embodiment in the range from about 0.05 to about 0.5 mm. The shim may have any length and width.

The term "waveform" may refer to a contiguous piece of thermally conductive material that is transformed from a planar object to a three-dimensional object. The waveform may be used to form one or more microchannels. The waveform may comprise a right angled corrugated insert which may be sandwiched between opposed planar sheets or shims. The right angled corrugated sheet may have rounded edges. In this manner one or more microchannels may be defined on three sides by the waveform and on the fourth side by one of the planar sheets or shims. The waveform may be made of any of the thermally conductive materials disclosed herein as being useful for making the microchannel reactor. These may include copper, aluminum, stainless steel, and the like. The thermal conductivity of the waveform may be about 1 W/m-K or higher.

Figure 20:
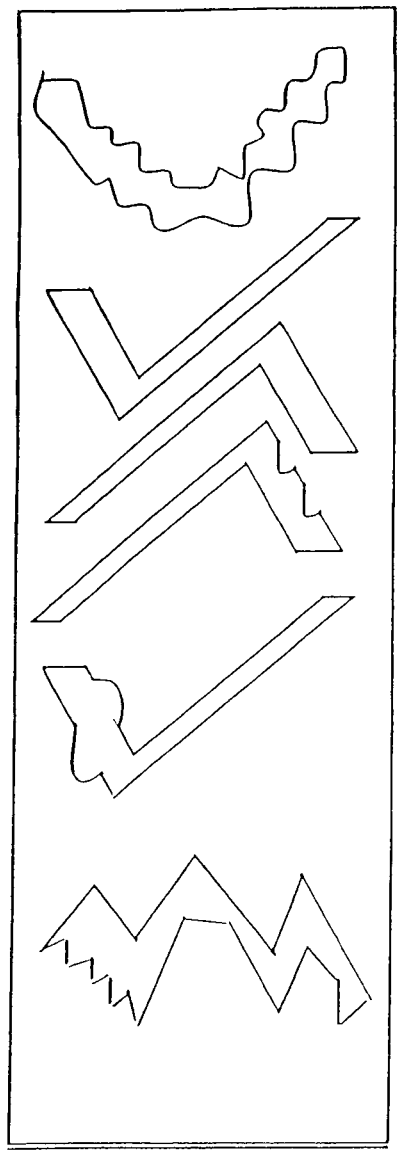
FIGS. 20 and 21 are schematic illustrations of surface features that may be used in the process microchannels and/or heat exchange channels employed in the microchannel reactor.
Figure 21:
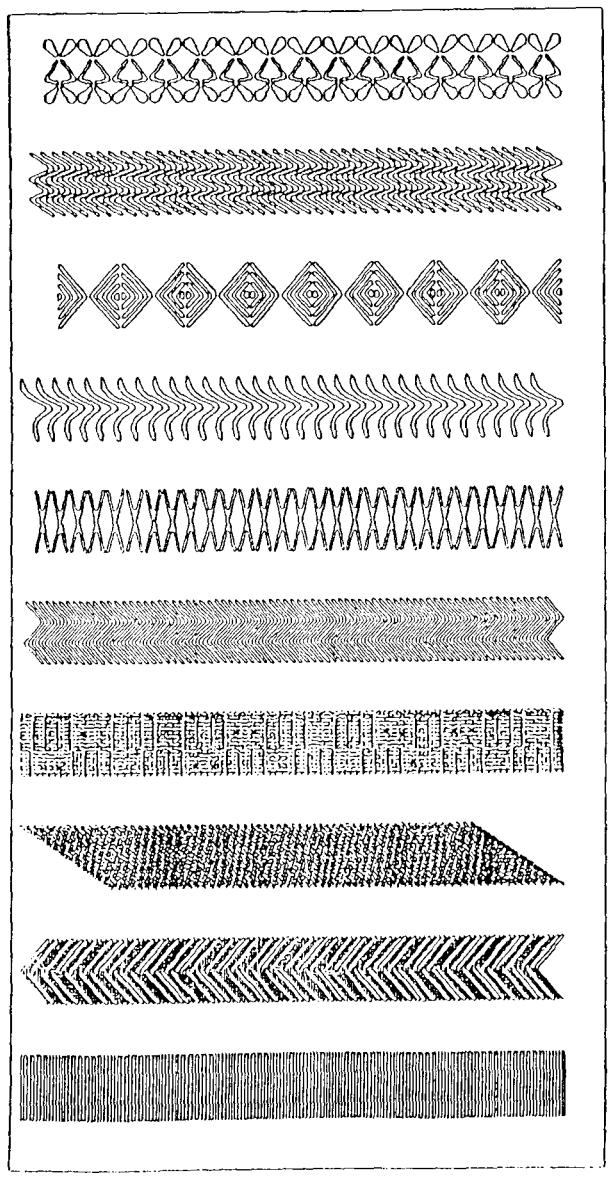

The term "surface feature" may refer to a depression in a channel wall and/or a projection from a channel wall that disrupts flow within the channel. Examples of surface feature designs that may be used are illustrated in FIGS. 20 and 21. The surface features may be in the form of circles, spheres, frustums, oblongs, squares, rectangles, angled rectangles, checks, chevrons, vanes, airfoils, wavy shapes, and the like, and combinations of two or more thereof. The surface features may contain subfeatures where the major walls of the surface features further contain smaller surface features that may take the form of notches, waves, indents, holes, burrs, checks, scallops, and the like. The surface features may have a depth, a width, and for non-circular surface features a length. The surface features may be formed on or in one or more of the interior walls of the process microchannels and/or heat exchange channels used in accordance with the inventive process. The surface features may be referred to as passive surface features or passive mixing features. The surface features may be used to disrupt flow (for example, disrupt laminar flow streamlines) and create advective flow at an angle to the bulk flow direction.

The term "heat exchange channel" may refer to a channel having a heat exchange fluid in it that provides heat and/or absorbs heat. The heat exchange channel may absorb heat from or provide heat to an adjacent channel (e.g., process microchannel) and/or one or more channels in thermal contact with the heat exchange channel. The heat exchange channel may absorb heat from or provide heat to channels that are adjacent to each other but not adjacent to the heat exchange channel. In one embodiment, one, two, three or more channels may be adjacent to each other and positioned between two heat exchange channels.

The term "heat transfer wall" may refer to a common wall between a process microchannel and an adjacent heat exchange channel where heat transfers from one channel to the other through the common wall.

The term "heat exchange fluid" may refer to a fluid that may give off heat and/or absorb heat.

The term "bulk flow direction" may refer to the vector through which fluid may travel in an open path in a channel.

The term "bulk flow region" may refer to open areas within a microchannel. A contiguous bulk flow region may allow rapid fluid flow through a microchannel without significant pressure drops. In one embodiment, the flow in the bulk flow region may be laminar. A bulk flow region may comprise at least about 5% of the internal volume and/or cross-sectional area of a microchannel, and in one embodiment from about 5% to about 100%, and in one embodiment from about 5% to about 99%, and in one embodiment about 5% to about 95%, and in one embodiment from about 5% to about 90%, and in one embodiment from about 30% to about 80% of the internal volume and/or cross-sectional area of the microchannel.

The terms "open channel" or "flow-by channel" or "open path" may refer to a channel (e.g., a microchannel) with a gap of at least about 0.01 mm that extends all the way through the channel such that fluid may flow through the channel without encountering a barrier to flow. The gap may extend up to about 10 mm.

The term "cross-sectional area" of a channel (e.g., process microchannel) may refer to an area measured perpendicular to the direction of the bulk flow of fluid in the channel and may include all areas within the channel including any surface features that may be present, but does not include the channel walls. For channels that curve along their length, the cross-sectional area may be measured perpendicular to the direction of bulk flow at a selected point along a line that parallels the length and is at the center (by area) of the channel. Dimensions of height and width may be measured from one channel wall to the opposite channel wall. These dimensions may not be changed by application of a coating to the surface of the wall. These dimensions may be average values that account for variations caused by surface features, surface roughness, and the like.

The term "open cross-sectional area" of a channel (e.g., process microchannel) may refer to an area open for bulk fluid flow in a channel measured perpendicular to the direction of the bulk flow of fluid flow in the channel. The open cross-sectional area may not include internal obstructions such as surface features and the like which may be present.

The term "superficial velocity" for the velocity of a fluid flowing in a channel may refer to the velocity resulting from dividing the volumetric flow rate of the fluid at the inlet temperature and pressure of the channel divided by the cross-sectional area of the channel.

The term "free stream velocity" may refer to the velocity of a stream flowing in a channel at a sufficient distance from the sidewall of the channel such that the velocity is at a maximum value. The velocity of a stream flowing in a channel is zero at the sidewall if a no slip boundary condition is applicable, but increases as the distance from the sidewall increases until a constant value is achieved. This constant value is the "free stream velocity."

The term "process fluid" may be used herein to refer to reactants, product and any diluent or other fluid that may flow in a process microchannel.

The term "reaction zone" may refer to the space within a microchannel wherein a chemical reaction occurs or wherein a chemical conversion of at least one species occurs. The reaction zone may contain one or more catalysts.

The term "yield" may refer to the number of moles of product exiting a microchannel reactor divided by the number of moles of a reactant entering the microchannel reactor.

The term "cycle" may refer to a single pass of the reactants through a microchannel reactor.

The term "graded catalyst" may refer to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel, or vice versa; or a lower concentration of catalytically active metal nearer the center (i.e., midpoint) of a process microchannel and a higher concentration nearer a process microchannel wall, or vice versa, etc. The thermal conductivity of a graded catalyst may vary from one location to another within a process microchannel. The surface area of a graded catalyst may be varied by varying size of catalytically active metal sites on a constant surface area support, or by varying the surface area of the support such as by varying support type or particle size. A graded catalyst may have a porous support where the surface area to volume ratio of the support is higher or lower in different parts of the process microchannel followed by the application of the same catalyst coating everywhere. A combination of two or more of the preceding embodiments may be used. The graded catalyst may have a single catalytic component or multiple catalytic components (for example, a bimetallic or trimetallic catalyst). The graded catalyst may change its properties and/or composition gradually as a function of distance from one location to another within a process microchannel. The graded catalyst may comprise rimmed particles that have "eggshell" distributions of catalytically active metal within each particle. The graded catalyst may be graded in the axial direction along the length of a process microchannel or in the lateral direction. The graded catalyst may have different catalyst compositions, different loadings and/or numbers of active catalytic sites that may vary from one position to another position within a process microchannel. The number of catalytically active sites may be changed by altering the porosity of the catalyst structure. This may be accomplished using a washcoating process that deposits varying amounts of catalytic material. An example may be the use of different porous catalyst thicknesses along the process microchannel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "carbonaceous material" may refer to any organic material or carbon containing material (e.g., biomass, solid waste, etc.) that may be converted to synthesis gas.

The term "synthesis gas" may refer to any gas that contains CO and $H_2$. Synthesis gas may be referred to as syngas.

The term "biomass" may refer to living or recently dead biological material that can be used as fuel. The term biomass may refer to plant matter grown for use as biofuel. The term biomass may include plant or animal matter used for production of fibers, chemicals or heat. Biomass may include biodegradable wastes that can be burnt as fuel. Biomass may comprise plants such as switchgrass, hemp, corn, poplar, willow, sugarcane, oil palm, and the like.

The term "char" may refer to a solid material that remains after gases have been driven out or released from a carbonaceous material. Char may be formed during the combustion of a carbonaceous material.

The term "tar" may refer to a viscous black liquid derived from the destructive distillation of a carbonaceous material.

The term "ash" may refer to the solid residue that remains after a carbonaceous material is burned.

The term "equilibrium limited chemical reaction" refers to a chemical reaction or a set of complementary reactions that do not proceed to completion due to the fact that the reactants and the product(s) reach a state of equilibrium. The following reactions, which may be used in the synthesis of methanol, are examples of equilibrium limited chemical reactions:

$$CO+H_2O \leftrightarrows CO_2+H_2 \qquad \text{Equation (1)}$$

$$CO_2+3H_2 \leftrightarrows CH_3OH+H_2O \qquad \text{Equation (2)}$$

$$CO+2H_2 \leftrightarrows CH_3OH \qquad \text{Equation (3)}$$

The synthesis of dimethyl ether by the following reaction is another example of an equilibrium limited chemical reaction:

$$3CO+3H_2 \leftrightarrows CH_3OCH_3+CO_2 \qquad \text{Equation (4)}$$

The synthesis of methane by the following reactions are additional examples of equilibrium limited chemical reactions:

$$CO+3H_2 \leftrightarrows CH_4+H_2O \qquad \text{Equation (5)}$$

$$CO+2H_2 \leftrightarrows CH_4+CO_2 \qquad \text{Equation (6)}$$

The term "reaction zone" refers to a space within the process microchannels wherein the reactants contact a catalyst at a particular temperature or within a particular temperature range and react.

The term "primary reactant" refers to one of the reactants in a chemical reaction. The primary reactant may or may not be present at the highest concentration of the reactants in the reactant composition. An example of a primary reactant is CO in the above-indicated reactions represented by Equations (1) and (3)-(6).

The term "conversion of the primary reactant" refers to the primary reactant mole change between the reactant composition and a product (i.e., intermediate product composition, final product composition, etc.) divided by the moles of the primary reactant in the reactant composition.

The term "conversion of CO" refers to the CO mole change between the reactant composition and product (i.e., intermediate product composition, final product composition, etc.) divided by the moles of CO in the reactant composition.

The term "equilibrium conversion" for a reactant refers to the conversion of the reactant when, for a given initial composition, the reaction is allowed to reach equilibrium at a particular temperature, pressure and final composition.

The term "approach to equilibrium" refers to the actual conversion of a reactant species (e.g., the primary reactant) obtained at a designated reaction temperature divided by the equilibrium conversion value for that reactant species at that reaction temperature. For example, if it were assumed that the equilibrium conversion value for CO in a reaction at 270° C. is 22%, and if it were assumed that the actual conversion for CO in that reaction at 270° C. was 12%, the approach to equilibrium would be 54.5% (100×12/22=54.5%).

The term "mm" may refer to millimeter. The term "nm" may refer to nanometer. The term "ms" may refer to millisecond. The term "µs" may refer to microsecond. The term "µm" may refer to micron or micrometer. The terms "micron" and "micrometer" have the same meaning and may be used interchangeably.

Unless otherwise indicated, all pressures are expressed in terms of absolute pressure.

The carbonaceous material that may be used in the inventive process may comprise any organic or carbon-containing material that can be gasified to produce synthesis gas. The carbonaceous material may comprise a food resource such as corn, soybean, and the like. The carbonaceous material may comprise a non-food resource. The non-food resource may be referred to as a second generation biofuel. The non-food resource may comprise any carbonaceous material not generally used as a food. The non-food resource may be referred to as a non-food carbonaceous material. Examples of the non-food carbonaceous materials that may be used may comprise coal (e.g., low grade coal, high grade coal, and the like), oil (e.g., crude oil, heavy oil, tar sand oil, and the like), biomass, solid wastes, or a mixture of two or more thereof. The non-food carbonaceous material may comprise municipal solid waste (MSW), hazardous waste, refuse derived fuel (RDF), tires, petroleum coke, trash, garbage, biogas from a digester, sewage sludge, animal waste (e.g., chicken manure, turkey manure, cow manure, horse manure, as well as other animal waste), agricultural waste, corn stover, switch grass, timber, wood cuttings, grass clippings, construction demolition materials, plastic materials (e.g., plastic waste), cotton gin waste, landfill gas, natural gas, and the like. The non-food carbonaceous material may comprise polyethylene or polyvinyl chloride. Mixtures of two or more of any of the foregoing may be used.

The carbonaceous material may be in the form of relatively large solid pieces and prior to step (A) these relatively large pieces may be shredded into smaller pieces using, for example, an auger.

The carbonaceous material may comprise water, and in at least one embodiment of the invention, it may be advantageous to remove some or all of the water prior to the gasification step (A) of the inventive process. This may be accomplished using conventional drying techniques.

The synthesis gas that is formed in the gasification step (A) of the inventive process may comprise a gaseous mixture that contains varying amounts of CO and $H_2$. In at least one embodiment of the inventive process, it is advantageous to use a synthesis gas during step (B)(I) with a molar ratio of $H_2$ to CO that may be in the range from about 0.5 to about 4, and in one embodiment in the range from about 1 to about 3, and in one embodiment in the range from about 1.5 to about 2.5, and in one embodiment in the range from about 1.8 to about 2.2. If the amount of $H_2$ produced during step (A) is not sufficient to provide for the $H_2$ to CO ratio specified above, additional amounts of $H_2$ may be added to the synthesis gas prior to step (B)(I) of the inventive process. The synthesis gas may also contain varying amounts of $CO_2$ and water as well as particulate solids and other contaminants. The $CO_2$, water, particulate solids and other contaminants may be separated out, or at least substantially separated out from the synthesis gas, prior to conducting step (B)(I) of the inventive process.

The inventive process, in its illustrated embodiments, will be described initially with respect to FIGS. 1-7. Referring to FIG. 1, the process 100 employs the use of gasifier 110 and microchannel reactor 200. The gasifier 110 may be used to convert a carbonaceous material (e.g., biomass, solid waste, etc.) to synthesis gas. The microchannel reactor 200 may be used to convert the synthesis gas to methane, methanol and/or dimethyl ether. In operation, the carbonaceous material enters the gasifier 110 through line 112. A gasification agent (e.g. steam, oxygen and/or air) enters the gasifier 110 through line 114. In the gasifier 110, the carbonaceous material and the gasification agent are heated and undergo a gasification reaction to form synthesis gas. The synthesis gas flows from the gasifier 110 into the microchannel reactor 200 through line 116. The synthesis gas flowing out of the gasifier 110 may be at an elevated temperature, for example, in excess of about 700° C., and as such it may be advantageous to reduce the temperature of the synthesis gas prior to entering the microchannel reactor 200. The reduced temperature may be at a level equal to or near the desired operating temperature in the first reaction zone 202 in the microchannel reactor 200. This may be accomplished using one or more heat exchangers in the line between the gasifier 110 and the microchannel reactor 200. These heat exchangers may be microchannel heat exchangers. The synthesis gas flowing out of the gasifier may contain undesirable levels of water, particulate solids, contaminants (e.g., sulfur, halogen, selenium, phosphorus, arsenic, nitrogen, carbon dioxide, and the like), and the like. The concentrations of these may be reduced using one or more gas-liquid sorption devices (which may employ the use of one or more ionic liquid sorbents), temperature swing adsorption (TSA) devices, pressure swing adsorption (PSA) devices, microchannel devises containing layers of nanofibers or nano-composite films, cyclones, condensers, and the like, in the line between the gasifier 110 and the microchannel reactor 200.

The microchannel reactor 200 may comprise one or more process microchannels. Each process microchannel contains reaction zones 202 and 204. The reaction zone 202 may be referred to as a first reaction zone. The reaction zone 204 may be referred to as a second or another reaction zone. A catalyst may be positioned in each reaction zone. The reaction zones 202 and 204 may be operated at different temperatures relative to one another. The same or different catalysts may be used in the reaction zones 202 and 204. Synthesis gas flows through the first reaction zone 202 and is converted to an intermediate product comprising the desired final product (i.e., methane, methanol and/or dimethyl ether) and unreacted synthesis gas. The intermediate product then flows through the second or another reaction zone 204 wherein additional amounts of unreacted synthesis gas are converted to the desired final product. The reaction zones 202 and 204 may be physically separated from one another by a non-reactive zone in which intermediate products may be cooled. Alternatively, the reaction zones 202 and 204 may not be physically separated, that is, the intermediate product may flow from the reaction zone 202 directly into the reaction zone 204. The heat exchanger may comprise one or more heat exchange channels adjacent to or in thermal contact with the one or more process microchannels. The heat exchange channels may be microchannels. One of the heat exchange channels or a group of two or more heat exchange channels may form a heat exchange zone. A heat exchange fluid flows in the heat exchange channels. The flow of the heat exchange fluid into and out of the microchannel reactor 200 is indicated by arrows 208 and 210, and 212 and 214, respectively. The process microchannels and heat exchange channels may be aligned in layers that are positioned side by side or stacked one above the other. The microchannel reactor 200 may include a header or manifold assembly to provide a passageway for the reactant synthesis gas to flow into the process microchannels with an even or substantially even distribution of flow to the process microchannels. The microchannel reactor 200 may include a product footer or manifold assembly to provide a passageway for product to flow out of the process microchannels in a rapid manner with a relatively high rate of flow. The microchannel reactor 200 may include a header or manifold assembly to provide a passageway for the heat exchange fluid to flow into the heat exchange channels with an even or substantially even distribution of flow of the heat exchange channels. The microchannel reactor 200 may include a heat exchange footer or manifold assembly to provide a passageway for heat exchange fluid to flow out of the heat exchange channels in a rapid manner with a relatively high rate of flow. The flow of process fluid through the microchannel reactor 200 may be in a vertical direction (e.g., from top to bottom), or in a horizontal direction, or in a direction that is at an angle with the horizontal. The product flows out of the microchannel reactor 200 as indicated by arrow 206. Although an advantage of the inventive process is that a high level of conversion of the synthesis gas may be obtained with one pass through the microchannel reactor 200, in one embodiment, unreacted synthesis gas from the product composition may be separated from the product composition and recycled back through the microchannel reactor 200. The unreacted synthesis gas may be recycled any number of times, for example one, two, three, four times, etc.

Figure 2:
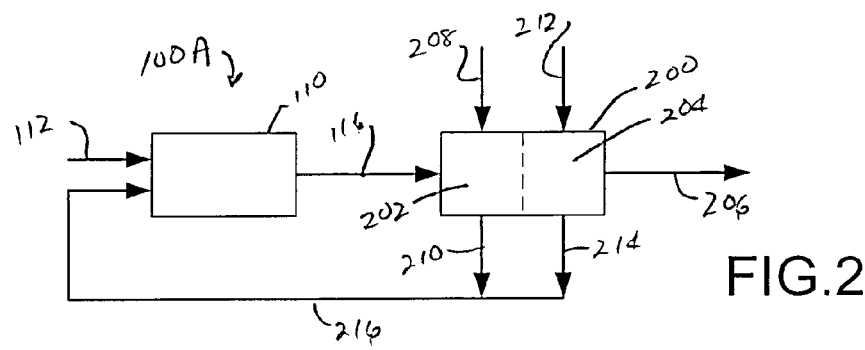
FIG. 2 is a flow sheet of a process that is the same as the process illustrated in FIG. 1 with the exception that steam, which is used as a heat exchange fluid in the microchannel reactor, is also used as a gasification agent in the gasifier.

The process 100A illustrated in FIG. 2 is the same as the process 100 illustrated in FIG. 1, with the exception that steam, which is used as the heat exchange fluid in the microchannel reactor 200, is also used as the gasification agent in the gasifier 110. The steam flows from the microchannel reactor 200 through lines 210, 214 and 216 to the gasifier 110. In the gasifier 110, the steam functions as a gasification agent during the gasification of the carbonaceous material.

Figure 3:
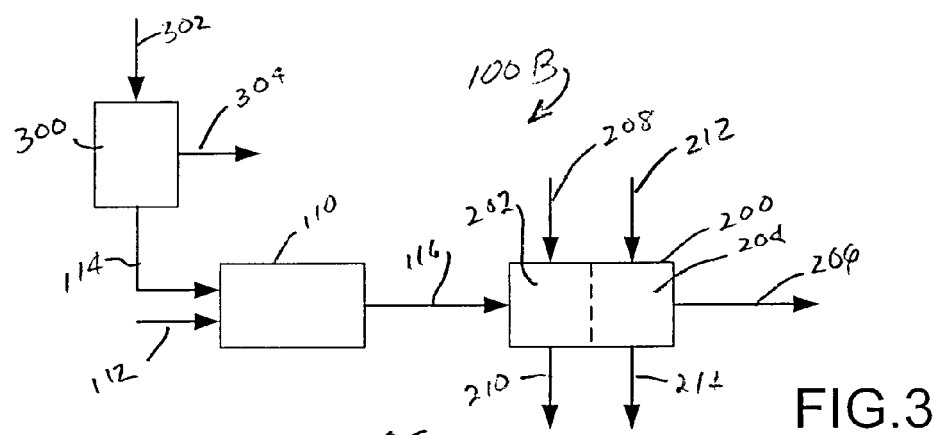
FIG. 3 is a flow sheet of a process that is the same as the process illustrated in FIG. 1 with the exception that the process includes the use of a nitrogen separator upstream of the gasifier. Nitrogen is separated from air in the nitrogen separator. The remaining oxygen enriched air or purified oxygen is used as the gasification agent in the gasifier.

The process 100B illustrated in FIG. 3 is the same as the process 100 illustrated in FIG. 1 with the exception that the process 100B includes a nitrogen separator 300. The nitrogen separator 300 may comprise any device suitable for separating nitrogen from air. For example, the nitrogen separator 300 may comprise an ionic liquid separator, a temperature swing adsorption (TSA) device or a pressure swing adsorption (PSA) device. The nitrogen separator 300 may comprise a microchannel device. In operation, air enters the nitrogen separator 300 through line 302 where it undergoes a separation process with the nitrogen being separated from the air. This results in the formation of an oxygen enriched air or purified oxygen. The nitrogen flows out of the nitrogen separator 300 through line 304. The oxygen enriched air or purified oxygen flows from the nitrogen separator 300 through line 114 into the gasifier 110. The oxygen enriched air or purified oxygen functions as a gasification agent in the gasifier 110. The carbonaceous material and the gasification agent undergo a gasification reaction to form synthesis gas. The synthesis gas flows from the gasifier 110 through line 116 to the microchannel reactor 200 where it undergoes a reaction to form methane, methanol and/or dimethyl ether as discussed above.

Figure 4:
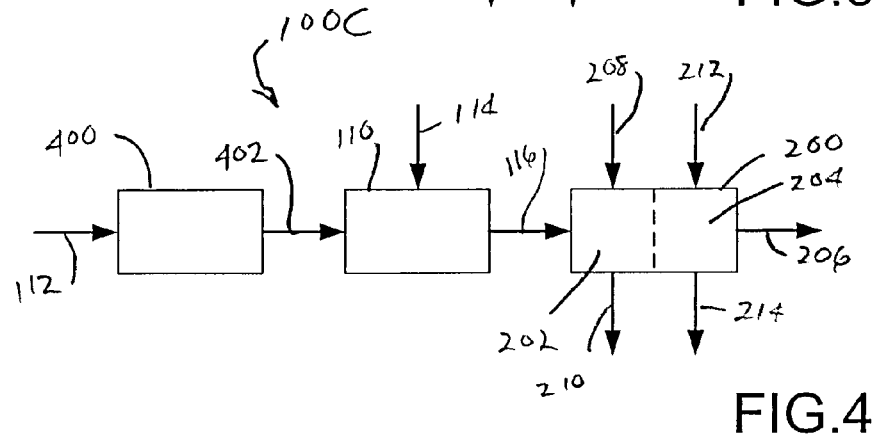
FIG. 4 is a flow sheet of a process that is the same as the process illustrated in FIG. 1 with the exception that the process illustrated in FIG. 4 employs the use of a pyrolysis reactor. The carbonaceous material is converted to pyrolytic oil in the pyrolysis reactor. The pyrolytic oil is used as the carbonaceous feed for the gasifier.

The process 100C illustrated in FIG. 4 is the same as the process 100 illustrated in FIG. 1, with the exception that the process 100C employs the use of pyrolysis reactor 400. In operation, the carbonaceous material enters the pyrolysis reactor 400 through line 112. In the pyrolysis reactor 400, the carbonaceous material undergoes a pyrolysis reaction with the result being the formation of a pyrolytic oil. The pyrolytic oil flows from the pyrolysis reactor 400 through line 402 to gasifier 110. A gasification agent enters the gasifier 110 through line 114. In the gasifier 110, the pyrolytic oil and the gasification agent are heated and undergo a gasification reaction to form synthesis gas. Synthesis gas flows from the gasifier 110 through line 116 to the microchannel reactor 200 where it undergoes a reaction to form methane, methanol and/or dimethyl ether as described above.

Figure 5:
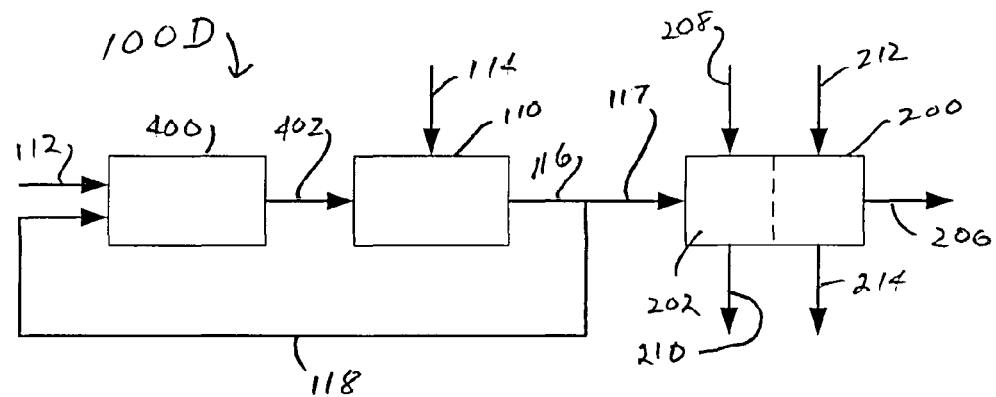
FIG. 5 is a flow sheet of a process that is the same as the process illustrated in FIG. 4 with the exception that liquid hydrocarbons, such as tar, are separated from the synthesis gas flowing out of the gasifier and recycled back to the pyrolysis reactor.

The process 100D illustrated in FIG. 5 is the same as the process 100C illustrated in FIG. 4, with the exception that liquid hydrocarbons, such as tar, are separated from the synthesis gas flowing out of the gasifier 110. These liquid hydrocarbons are recycled back to the pyrolysis reactor 400 from line 116 through line 118. The recycled liquid hydrocarbons, and the carbonaceous material entering the pyrolysis reactor 400 through line 112, are combined and subjected to pyrolysis in the pyrolysis reactor 400 resulting in the formation of pyrolytic oil. The pyrolytic oil flows from the pyrolysis reactor 400 through line 402 to the gasifier 110 wherein it is combined with a gasification agent which enters the gasifier 110 through line 114. The pyrolytic oil and gasification agent are heated in the gasifier 110 and undergo a gasification reaction to form synthesis gas. The synthesis gas flows from the gasifier 110 through line 116 to the microchannel reactor 200. In the microchannel reactor 200, the synthesis gas is converted to methane, methanol and/or dimethyl ether as described above.

Figure 6:
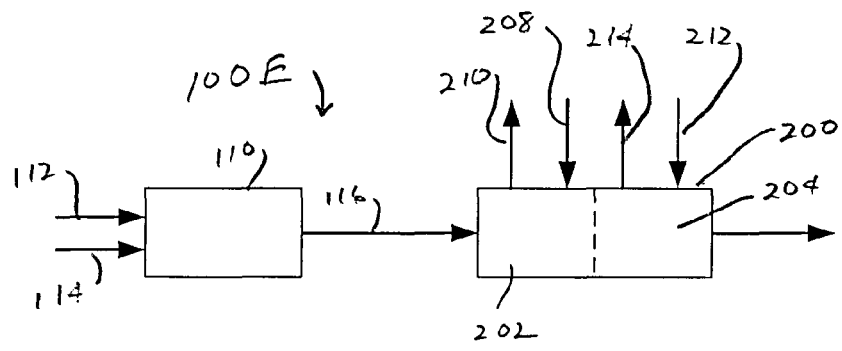
FIG. 6 is a flow sheet of a process that is the same as the process illustrated in FIG. 1 with the exception that the heat exchange fluid flowing through the microchannel reactor flows in a direction that is counter-current to the flow of process fluid.

The process 100E illustrated in FIG. 6 is the same as the process 100 illustrated in FIG. 1 with the exception that the heat exchange fluid flows through the heat exchange channels in the microchannel reactor 200 in a direction that is counter-current to the direction of process fluid flowing through the one or more process microchannels in the microchannel reactor. Alternatively, the flow of heat exchange fluid may be co-current relative to the flow of process fluid. In contrast, in the process 100 illustrated in FIG. 1, the heat exchange fluid flows through the heat exchange channels in the microchannel reactor 200 in a direction that is cross-current relative to the flow of process fluid in the one or more process microchannels in the microchannel reactor.

Figure 7:
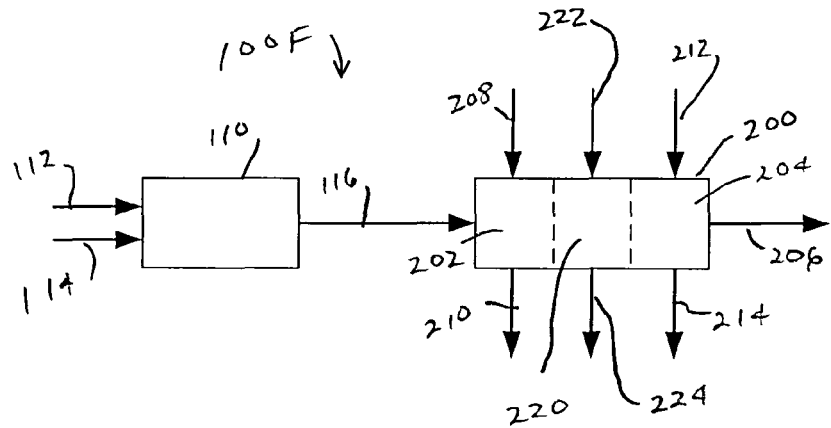
FIG. 7 is a flow sheet of a process that is the same as the process illustrated in FIG. 1 with the exception that the process microchannels in the microchannel reactor shown in FIG. 7 contain three reaction zones while the process microchannels in the microchannel reactor shown in FIG. 1 contain two reaction zones.

The process 100F illustrated in FIG. 7 is the same as the process 100 illustrated in FIG. 1, with the exception that the one or more process microchannels in the microchannel reactor 200 illustrated in FIG. 7 contains three reaction zones, namely, reaction zones 202, 204 and 220. These reaction zones may be referred to as the first reaction zone 202, the second or another reaction zone 204, and an additional reaction zone 220. The process illustrated in FIG. 7 involves flowing the synthesis gas from line 116 in the one or more process microchannels in the microchannel reactor through first reaction zone 202 to form an intermediate product composition comprising synthesis gas and the desired product (i.e., methane, methanol, and/or dimethyl ether), flowing the intermediate product composition formed in the first reaction zone 202 through the additional reaction zone 220 to form another intermediate product composition comprising synthesis gas and the desired product, and then flowing the another intermediate product composition through the second or another reaction zone 204 to form the final desired product (i.e., methane, methanol and/or dimethyl ether). Heat exchange fluid flows through heat exchange channels adjacent to or in thermal contact with the one or more process microchannels reaction zone 202 in a cross-flow direction as indicated by arrows 208 and 210, and 222 and 224, and 212 and 214.

The reaction to form dimethyl ether is shown above in Equation (4). This reaction is highly exothermic and thus is particularly suitable for being conducted in a microchannel reactor where it is possible to provide enhanced temperature control. On the other hand, in conventional (i.e., non-microchannel) reactors, this reaction often tends to runaway resulting in possible coking and catalyst deactivation. When conducting this reaction in a microchannel reactor it is possible to optimize single pass-through product yields at high throughputs.

The $CO_2$ produced in the process for making dimethyl either may be reacted with methane pursuant to the following equation:

$$CO_2 + CH_4 \rightarrow 2CO + 2H_2$$

This reaction may be conducted in a microchannel reactor. This reaction is endothermic, and thus requires heat input, for example, by combusting methane. This may be done in the heat exchange channels of the microchannel reactor. The reaction may be conducted in the presence of a catalyst. Examples of the catalysts that may be used may be catalysts which comprise La, Pt, Fe, Ni, Ru, Rh, In, Ir, W, and/or an oxide thereof, or a mixture of two or more thereof. The catalyst may further comprise MgO, $Al_2O_3$, $SiO_2$, $TiO_2$, or a mixture of two or more thereof. The catalyst may comprise nickel supported on alumina. The product from this reaction may be recycled to the microchannel reactor 200 where it may be combined with the synthesis gas produced in the gasifier 110 and used to optimize the $CO:H_2$ ratio flowing into the microchannel reactor 200. This recycle step may be advantageous since it provides for the reduction or elimination of emissions of $CO_2$ which has been identified as a greenhouse gas.

The gasification step (A) of the inventive process involves converting the carbonaceous material to synthesis gas by reacting the carbonaceous material at a temperature of at least about 700° C. with a gasification agent. The gasification agent may comprise oxygen, air and/or steam. The gasification step (A) may be conducted at a temperature of at least about 800° C., and in one embodiment at a temperature of at least about 900° C., and in one embodiment at a temperature of at least about 1000° C., and in one embodiment at a temperature of at least about 1100° C., and in one embodiment at a temperature of at least about 1200° C. The gasification step (A) may be conducted at a temperature in the range from about 700° C. to about 2500° C., and in one embodiment in the range from about 800° C. to about 2200° C., and in one embodiment in the range from about 900° C. to about 2000° C., and in one embodiment in the range from about 1000° C. to about 1800° C., and in one embodiment in the range from about 1100° C. to about 1800° C., and in one embodiment in the range from about 1200° C. to about 1800° C., and in one embodiment in the range from about 1300° C. to about 1500° C. The elevated temperatures used during step (A) distinguish it from biological processes such as anaerobic digestion that produce biogas.

While not wishing to be bound by theory, it is believed that during step (A) of the inventive process, the carbonaceous material may undergo the following processes:

1. A pyrolysis (or devolatilization) process may occur as the carbonaceous material heats up. Volatiles may be released and char may be produced, resulting in, for example, up to about 70% by weight loss. The process may be dependent on the properties of the carbonaceous material. These properties may determine the structure and composition of the char.

2. A combustion process may occur as the volatile products and some of the char reacts with oxygen to form carbon dioxide and carbon monoxide. This may provide heat for the subsequent gasification reactions.

3. Reaction of the char with carbon dioxide and steam to produce carbon monoxide and hydrogen.

4. A reversible gas phase water gas shift reaction may reach equilibrium at the temperatures in the gasifier. This may result in balancing the concentrations of carbon monoxide, steam, carbon dioxide and hydrogen $$CO + H_2O \leftrightarrow CO_2 + H_2$$

With these processes, a limited amount of oxygen may be introduced into the gasifier to allow some of the carbonaceous material to be burned to produce carbon monoxide and energy in a first reaction. The molar ratio of oxygen to carbon may be in the range from about 0.01:1 to about 5:1, and in one embodiment in the range from about 0.2:1 to about 2:1, and in one embodiment in the range from about 0.5:1 to about 1.5:1, and in one embodiment in the range from about 0.5:1 to about 1.2:1, and in one embodiment about 1:1. This reaction may be used to drive a second reaction that converts further carbonaceous material to hydrogen and additional carbon monoxide.

The gasification step (A) may be conducted in a counter-current fixed bed gasifier, a co-current fixed bed gasifier, a fluidized bed gasifier, or an entrained flow gasifier. The counter-current fixed bed gasifier may comprise a fixed bed of carbonaceous material through which the gasification agent (e.g., steam, oxygen and/or air) flows in counter-current configuration. Ash may be removed either dry or as a slag. The slagging gasifiers may require a higher ratio of steam and oxygen to carbon in order to reach temperatures higher than the ash fusion temperature. The carbonaceous material may require a high mechanical strength and a non-caking composition so that it may form a permeable bed. The throughput for this type of gasifier may be relatively low. Thermal efficiency may be high as the gas exit temperature may be relatively low. Tar and methane may be produced with this process.

The co-current fixed bed gasifier is similar to the counter-current type, with the exception that the gasification agent flows in co-current configuration with the carbonaceous material. Heat may need to be added to the upper part of the bed, either by combusting small amounts of the carbonaceous material or from external heat sources. The synthesis gas may leave the gasifier at a high temperature. Most of this heat may be transferred to the gasification agent added in the top of the bed to provide for energy efficiency. Tars may pass through a hot bed of char in this configuration. However, the tar levels may be lower than with the counter-current type.

In the fluidized bed gasifier, the carbonaceous material may be fluidized in the gasification agent. Ash may be removed dry or as heavy agglomerates that defulidize. The temperature may be relatively low in dry ash gasifiers and, as such, the carbonaceous material may be relatively highly reactive; low-grade coals may be particularly suitable. The agglomerating gasifiers may operate at slightly higher temperatures, and may be suitable for higher rank coals. Carbonaceous material throughput may be higher than for the fixed bed, but not as high as for the entrained flow gasifier. The conversion efficiency may be rather low due to elutriation of carbonaceous material. Recycle or subsequent combustion of solids may be used to increase conversion. Fluidized bed gasifiers may be useful for carbonaceous materials that form highly corrosive ash that may damage the walls of slagging gasifiers.

In the entrained flow gasifier a dry pulverized solid carbonaceous material, an atomized liquid carbonaceous material, or a slurry of the carbonaceous material may be gasified with oxygen or air in co-current flow. The gasification reactions may take place in a dense cloud of very fine particles. Most coals may be suitable for this type of gasifier because of the high operating temperatures and because the coal particles may be well separated from one another. The high temperatures and pressures may also mean that a higher throughput may be achieved, however thermal efficiency may be somewhat lower as the gas may be cooled before it can be cleaned. The high temperatures may also mean that tar and methane may not be present in the product synthesis gas; however the oxygen requirement may be higher than for the other types of gasifiers. Entrained flow gasifiers may remove a major part of the ash as a slag as the operating temperature may be above the ash fusion temperature. A smaller fraction of the ash may be produced either as a very fine dry fly ash or as a black colored fly ash slurry. Some carbonaceous materials, in particular certain types of biomasses, may form slag that is corrosive for ceramic inner walls that may serve to protect the gasifier outer wall. However, some entrained bed types of gasifiers may not possess a ceramic inner wall but may have an inner water or steam cooled wall covered with partially solidified slag. These types of gasifiers may not suffer from corrosive slags. Some carbonaceous materials may have ashes with very high ash fusion temperatures. In this case limestone may be mixed with the fuel prior to gasification. Addition of limestone may suffice for lowering the fusion temperatures. The carbonaceous material particles may be smaller than for other types of gasifiers. This may mean that the carbonaceous material may be pulverized, which may require more energy than for the other types of gasifiers.

The gasification step (A) may be conducted in a molten metal reactor. In the molten metal reactor, the carbonaceous material and steam contact molten metal and react to form the synthesis gas. The molten metal may comprise a reactive metal (Me) that reacts with a first portion of the steam entering the reactor according to the following equation:

$$xMe+yH_2O \rightarrow yH_2+Me_xO_y$$

The carbonaceous material may react with a second portion of the steam to form carbon monoxide and hydrogen. The reactive metal may have an oxygen affinity that is similar to the oxygen affinity of hydrogen. The reactive metal may comprise one or more of the following metals or their alloys: germanium, iron, zinc, tungsten, molybdenum, indium, tin, cobalt or antimony. The reactive metal may be at least partially dissolved in a second metal or mixture of metals. The metal into which the reactive metal is dissolved may be referred to as a diluent metal. The diluent metal may also be reactive with steam, in which case it may be selected from the reactive metals disclosed above, provided that the diluent metal is less reactive than the reactive metal. The diluent metal may comprise one or more of nickel, copper, ruthenium, rhodium, palladium, silver, cadmium, rhenium, osmium, iridium, platinum, gold, mercury, lead, bismuth, selenium or tellurium. More than one diluent metal may be utilized in the molten metal mixture. In one embodiment, the reactive metal may comprise iron, and the diluent metal may comprise tin. Molten metal reactors that may be used to convert the carbonaceous material to synthesis gas may include the molten metal reactors disclosed in U.S. Pat. Nos. 7,232,472 B2; 6,685,754B2; 6,682,714B2; and 6,663,681B2; which are incorporated herein by reference.

The gasification step (A) may be conducted in a plasma based gasification system. With such a system, the carbonaceous material may be fed into a plasma converter which may comprise a sealed, stainless steel vessel filled with either nitrogen or ordinary air. An electric current (e.g., a 650-volt electrical current) may be passed between two electrodes; this removes electrons from the nitrogen or air and creates plasma. A constant flow of electricity through the plasma maintains a field of intense energy powerful enough to disintegrate the carbonaceous material into its component elements. The byproducts may comprise a glass-like substance, which may be used as a raw material for high-strength asphalt or household tiles, and synthesis gas. The synthesis gas may leave the plasma converter at a high temperature, e.g., about 2200° F. (1204° C.). The synthesis gas may then be fed into a cooling system which generates steam. This steam may be used to drive turbines which produce electricity, part of which may be used to power the plasma converter, while the rest may be used for the plant's heating or electrical needs, or sold back to the utility grid. The synthesis gas may then be advanced to the microchannel reactor 200.

The processes for converting synthesis gas to methane, methanol and/or dimethyl ether in the microchannel reactor 200 may comprise exothermic equilibrium limited chemical reactions. These reactions are subjected to cooling in the microchannel reactor 200. The cooling provided by the microchannel reactor 200 occurs as a result of the flow of a heat exchange fluid (e.g., steam) through heat exchange channels adjacent to or in thermal contact with the process microchannels in the microchannel reactor 200. Each of the process microchannels contains a first reaction zone 202 and a second or another reaction zone 204. The first reaction zone 202 may be located near the entrances to the process microchannels. The second or another reaction zone 204 may be located near the outlets of the process microchannels. One or more additional reaction zones 220 may be positioned between the first reaction zone 202 and the second or another reaction zone 204. The one or more additional reaction zones 220 may comprise any desired number of reaction zones, for example, one, two, three, four, five, six, seven, eight, nine, ten, or more additional reaction zones. The temperature in the first reaction zone 202 may be higher than the temperature in the second or another reaction zone 204. The temperature in each additional reaction zone 220 may be progressively cooler as the additional reaction zones 220 are positioned further downstream from the first reaction zone 202.

In the first reaction zone 202 the inventive process is conducted under a first set of reaction conditions suitable for producing a first equilibrium product. The composition of the first equilibrium product is dependent upon the reaction process, the reaction temperature and the composition of the reactant composition. The composition of the intermediate product that is actually formed in the first reaction zone is dependent upon the degree of conversion of the primary reactant (i.e., CO). The approach to equilibrium conversion for the primary reactant in the first reaction zone 202 may be at least about 5%, and in one embodiment at least about 20%, and in one embodiment at least about 40%, and in one embodiment at least about 50%, and in one embodiment at least about 60%, and in one embodiment at least about 70%, and in one embodiment at least about 80%, and in one embodiment at least about 90%. The approach to equilibrium conversion for the primary reactant may range from about 5% to about 99%, and in one embodiment from about 20% to about 98%, and in one embodiment from about 40% to about 98%, and in one embodiment from about 50% to about 95%, and in one embodiment from about 60% to about 95%, and in one embodiment from about 75% to about 95%, and in one embodiment from about 80% to about 95%. The intermediate product formed in the first reaction zone 202 contains the desired product (i.e., methane, methanol, and/or dimethyl ether) for the reaction as well as unreacted reactants. For example, if the reaction is the methanol synthesis reaction represented by Equation (3), the desired product is $CH_3OH$, and the intermediate product also contains CO and $H_2$. The equilibrium conversion value for the conversion of CO may be, for example, about 42%, and the actual conversion of CO obtained in the first reaction zone with the inventive process may be, for example, about 22%. The approach to equilibrium would thus be 52.4% ($100\times22/42=52.4\%$). For the methanol synthesis reaction indicated above, the conversion of CO that is achieved in the first reaction zone may range from about 5 to about 50%, and in one embodiment from about 10 to about 40%.

In the second or another reaction zone 204 the process is conducted under a second or another set of reaction conditions suitable for producing a second or another equilibrium product. The composition of the second or another equilibrium product is also dependent upon the reaction process, the reaction temperature and the reactants in the intermediate product composition entering the second or another reaction zone. The composition of the product that is formed in the second or another reaction zone is dependent upon the degree of conversion of the primary reactant. The approach to equilibrium conversion for the primary reactant (i.e., CO) in the second or another reaction zone 204 may be at least about 5%, and in one embodiment about 20%, and in one embodiment at least about 40%, and in one embodiment at least about 50%, and in one embodiment at least about 60%, and in one embodiment at least about 70%, and in one embodiment at least about 80%, and in one embodiment at least about 90%. The approach to equilibrium conversion for the primary reactant may range from about 5% to about 99%, and in one embodiment from about 20% to about 98%, and in one embodiment from about 40% to about 98%, and in one embodiment from about 50% to about 95%, and in one embodiment from about 60% to about 95%, and in one embodiment from about 75% to about 95%, and in one embodiment from about 80% to about 95%. The product formed in the second or another reaction zone 204 contains the desired product (i.e., methane, methanol and/or dimethyl ether) for the reaction as well as unreacted reactants. For example, if the reaction is the above-indicated methanol synthesis reaction represented by Equation (3), the desired product is $CH_3OH$, and the final product composition may contain $H_2$ and CO. The equilibrium value for the conversion of CO for the reaction in the second or another reaction zone 204 may be, for example, about 72%, and the actual conversion of CO obtained in the second or another reaction zone 204 with the inventive process may be, for example, about 52%, with the approach to equilibrium thus being about 72.2% ($100\times52/72=72.2\%$). For the methanol synthesis reaction, the rate of reaction is lower in the second or another reaction zone 204, but the conversion of CO increases. For example, for the above-indicated methanol synthesis reaction, the conversion of CO that may be achieved in the second or another reaction zone 204 may be from about 10 to about 90%, and in one embodiment about 20 to about 80%.

The approach to equilibrium for the primary reactant (i.e., CO) in the first reaction zone 202 may be the same or about the same as the approach to equilibrium for the primary reactant in the second or another reaction zone 204. The approach to equilibrium in the first reaction zone 202 may be within about 50% of the approach to equilibrium in the second or another reaction zone 204, and in one embodiment within about 75%, and in one embodiment within about 95%, and in one embodiment within about 98%.

As indicated above, one or more additional reaction zones 220 may be employed between the first reaction zone 202 and the second or another reaction zone 204. In these additional reaction zones the process is conducted under one or more sets of reaction conditions suitable for producing one or more additional equilibrium products. The composition of the intermediate product produced in each of these additional reaction zones 220 is dependent upon the reaction process, the temperature within the additional reaction zones, and the composition of the intermediate product entering the additional reaction zones. The composition of each of the intermediate products produced in these additional reaction zones is dependent upon the degree of conversion of the primary reactant. The approach to equilibrium for each of these one or more additional reaction zones may be at least about 5%, and in one embodiment at least about 20%, and in one embodiment at least about 40%, and in one embodiment at least about 50%, and in one embodiment at least about 60%, and in one embodiment at least about 70%, and in one embodiment at least about 80%, and in one embodiment at least about 90%. The approach to equilibrium conversion for the primary reactant may range from about 5% to about 99%, and in one embodiment from about 20% to about 98%, and in one embodiment from about 40% to about 98%, and in one embodiment from about 50% to about 95%, and in one embodiment from about 60% to about 95%, and in one embodiment from about 75% to about 95%, and in one embodiment from about 80% to about 95%.

The approach to equilibrium for the primary reactant (i.e., CO) in the first reaction zone 202, the approach to equilibrium for the primary reactant in the second or another reaction zone 204, and the approach to equilibrium for the primary reactant in the one or more additional reaction zones 220 may be the same or about the same. The approach to equilibrium in the first reaction zone 202 may be within about 50% of the approach to equilibrium in the second or another reaction zone 204 and the approach to equilibrium in the one or more additional reaction zones 220, and in one embodiment within about 75%, and in one embodiment within about 95%, and in one embodiment within about 98%.

Optionally, the reactants and intermediate products may be cooled in heat exchange zones positioned between the reaction zones. Product fractions may be separated out between one or more of the reaction zones. This is shown in WO 2008/030467 A2, which is incorporated herein by reference. These heat exchange zones may be located within the process microchannels and may be characterized as open sections of the process microchannels not containing catalyst. The temperature of the reactants and intermediate products may be adjusted in these heat exchange zones to the operating temperature in the next adjacent downstream reaction zone.

In an alternate embodiment, the separate reaction zones may be positioned in separate microchannel reactors. The product formed in each microchannel reactor maybe cooled prior to being advanced to the next downstream microchannel reactor. Product fractions may be separated out between each of the microchannel reactors.

As conversion approaches 100% in an equilibrium limited chemical reaction, the efficiency of the process drops off significantly due to the fact that the approach to equilibrium is asymptotic. Thus, in a particularly advantageous embodiment, the approach to equilibrium for the conversion of the primary reactant in each reaction zone may be from about 5% to about 99%, and in one embodiment about 20% to about 98%, and in one embodiment about 40% to about 98%, and in one embodiment from about 50% to about 95%, and in one embodiment about 60% to about 95%. The approach to equilibrium for the conversion of the primary reactant may be from about 75% to about 95%, and in one embodiment from about 80% to about 95%.

There may or may not be a physical separation between the reaction zones in the process microchannels. The same catalyst may be used in each reaction zone, where the catalyst extends continuously between the reaction zones. There may be different temperatures maintained in the reaction zones by the use of controlling the heat exchange fluid and/or fluid properties in the heat exchange channels. For example, a higher heat exchange fluid flowrate may be used in some heat exchange channels. If partial or full boiling of the heat exchange fluid is employed as a means to remove heat, the pressure in individual or groups of heat exchange channels, i.e., heat exchange zones, may be reduced to modify the local boiling temperature and thus corresponding temperature in the adjacent reaction zone. The local heat exchange channel temperature may be varied by changing the pressure in the heat exchange channel.

The microchannel reactor 200 may have a high surface-to-volume ratio and as a result exhibits enhanced heat and mass transfer rates. This permits operation of the inventive process with very close temperature control. With the inventive process it is possible to tailor the temperature profile within the microchannel reactor to achieve high product yields. In one embodiment of the inventive process it is possible to achieve enhanced heat exchange (e.g., enhanced cooling) as a result of the use of the microchannel reactor which permits the use of high activity catalysts that are difficult to use in conventional reactors.

Figure 8:
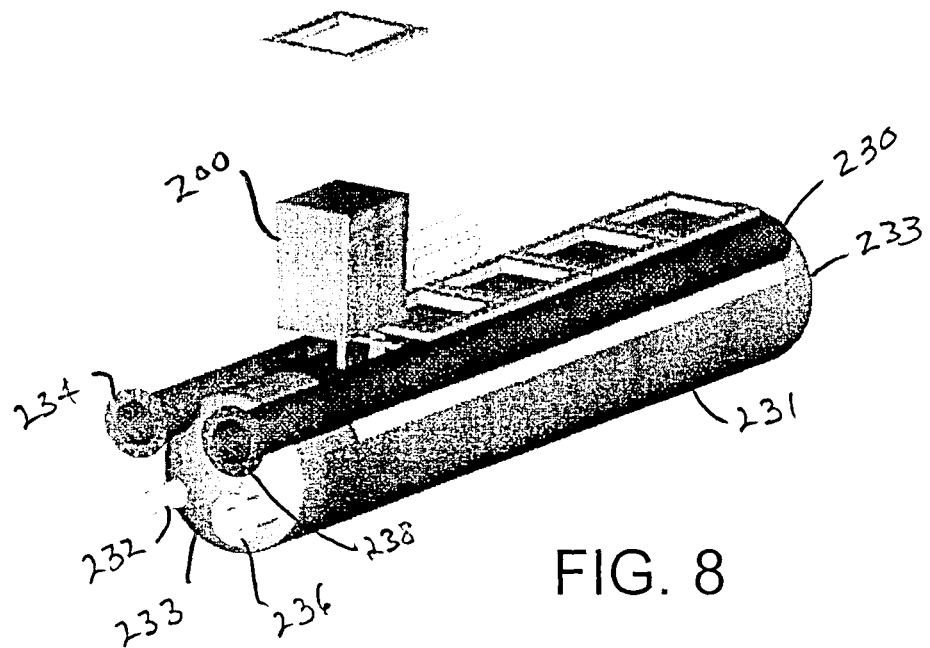
FIGS. 8 and 9 are schematic illustrations of a vessel used for housing a plurality of the microchannel reactors shown in FIG. 1.
Figure 9:
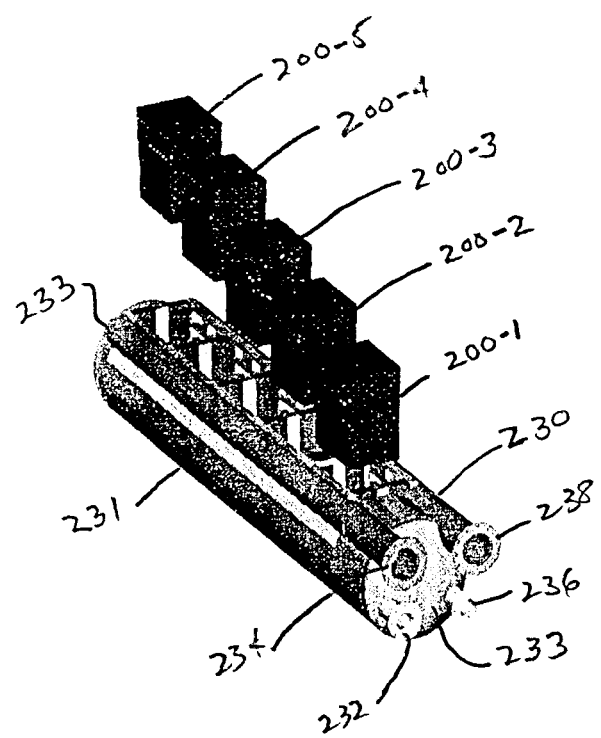

One or more of the microchannel reactors 200 may be housed in vessel 230, which has the construction illustrated in FIGS. 8 and 9. Referring to FIGS. 8 and 9, the vessel 230 contains five microchannel reactors 200. These are identified in FIG. 9 as microchannel reactors 200-1, 200-2, 200-3, 200-4 and 200-5. Although five microchannel reactors are disclosed in the drawings, it will be understood that the vessel 230 may contain any desired number of microchannel reactors. For example, the vessel 200 may contain from about 1 to about 1000 microchannel reactors 200, and in one embodiment from 1 to about 750, and in one embodiment from 1 to about 500, and in one embodiment from 1 to about 250, and in one embodiment from 1 to about 100, and in one embodiment from about 1 to about 50, and in one embodiment from 1 to about 20 microchannel reactors 200. The vessel 230 may be a pressurizable vessel. The vessel 230 includes inlets 234 and 238, and outlets 232 and 236.

Inlet 234 is connected to a manifold which is provided for flowing synthesis gas to process microchannels in the microchannel reactors 200. The inlet 238 is connected to a manifold which is provided for flowing heat exchange fluid (e.g., steam) to heat exchange channels in the microchannel reactors 200. The outlet 232 is connected to a manifold which provides for the flow of product from the process microchannels in the microchannel reactors 200. The outlet 236 is connected to a manifold to provide for the flow of the heat exchange fluid out of the heat exchange channels in the microchannel reactors 200.

The vessel 230 may be constructed using any suitable material sufficient for operating under the pressures and temperatures required for operating the microchannel reactors 200. For example, the shell 231 and heads 233 of the vessel 230 may be constructed of cast steel. The flanges, couplings and pipes may be constructed of 316 stainless steel. The vessel 230 may have any desired diameter, for example, from about 10 to about 1000 cm, and in one embodiment from about 50 to about 300 cm. The axial length of the vessel 230 may be of any desired value, for example, from about 0.5 to about 50 meters, and in one embodiment from about 1 to about 20 meters.

The microchannel reactors 200 may comprise a plurality of process microchannels and heat exchange channels stacked one above the other or positioned side-by-side. The microchannel reactors 200 may be in the form of cubic blocks. Each of these cubic blocks may have a length, width and height, the length being in the range from about 10 to about 1000 cm, and in one embodiment in the range from about 20 to about 200 cm. The width may be in the range from about 10 to about 1000 cm, and in one embodiment in the range from about 20 to about 200 cm. The height may be in the range from about 10 to about 1000 cm, and in one embodiment in the range from about 20 to about 200 cm.

The microchannel reactors 200 as well as the vessels 230 may be sufficiently small and compact so as to be readily transportable. As such, these reactors and vessels along with the other equipment used in the inventive process may be readily transported to remote locations, and used to convert carbonaceous waste products such as solid waste (e.g., trash, garbage, etc.), biomass, etc. to methane, methanol and/or dimethyl ether on a relatively small scale, for example, from about 50 to about 500 cubic meters of gas or liters of liquid per day. Alternatively, the vessels 230 may be relatively large and the number of microchannel reactors 200 in the vessels may be relatively high to provide for high volume production levels. For example, the inventive process may be adapted to convert a carbonaceous material such as municipal solid waste to methane, methanol and/or dimethyl ether on a relatively large scale, for example thousands or tens of thousands of cubic meters of gas or liters of liquid per day.

The microchannel reactors 200 may each comprise a plurality of repeating units, each of which includes one or more process microchannels and one or more heat exchange channels. The repeating units that may be used may include the repeating units 240, 240A, 240B and 240C illustrated in FIGS. 10-13, respectively. The microchannel reactors 200 may comprise from about 1 to about 1000 of the repeating units 240, 240A, 240B or 240C, and in one embodiment from about 10 to about 500 of such repeating units. The catalyst used in the repeating units 240-240C may be in any form including the various catalyst structured forms described below.

Figure 10:
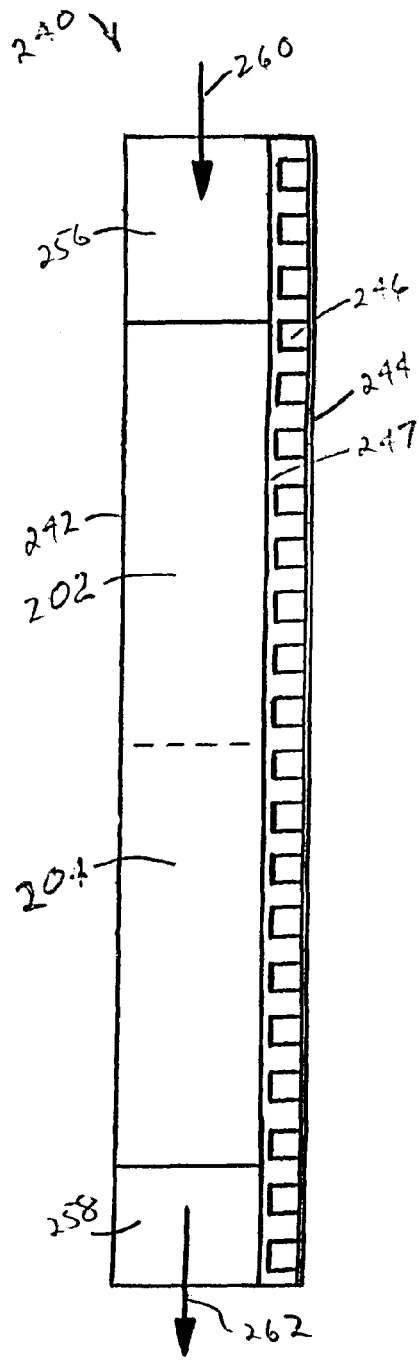
FIGS. 10-13 are schematic illustrations of repeating units that may be used in the microchannel reactor illustrated in FIG. 1. Each of the repeating units illustrated in FIGS. 10-13 includes a process microchannel that contains two reaction zones. One of the reaction zones may be referred to as the first reaction zone, and the other reaction zone may be referred to as the second or another reaction zone. The second or another reaction zone is downstream of the first reaction zone. Each repeating unit contains one or more heat exchange channels adjacent to the process microchannel. Heat exchange fluid flowing in the heat exchange channels illustrated in FIG. 10 flows in a direction that is cross-current relative to the flow of process fluid in the process microchannel. Heat exchange fluid flowing in the heat exchange channels illustrated in FIG. 11 flows in a direction that is counter-current to the flow of process fluid in the process microchannel. The heat exchange channels illustrated in FIGS. 12 and 13 provide for the flow of heat exchange fluid in a direction that is cross-current relative to the flow of process fluid in the process microchannel. The repeating units illustrated in FIGS. 12 and 13 provide for more heat exchange channels in the second or another reaction zones as compared to the first reaction zones. Tailored heat exchange profiles may be provided with each of these repeating units by controlling the number of heat exchange channels adjacent to the reaction zones. For example, more cooling channels may be provided in the second or another reaction zone as compared to the first reaction zone. This is shown in FIGS. 12 and 13. The heat exchange profile may also be tailored by controlling the flow rate of heat exchange fluid in the heat exchange channels. For example, a relatively high rate of flow of heat exchange fluid in the heat exchange channels adjacent to the second or another reaction zone may be used in combination with a relatively low rate of flow of heat exchange fluid in the heat exchange channels adjacent to the first reaction zones.

Repeating unit 240 is illustrated in FIG. 10. Referring to FIG. 10, process microchannel 242 is positioned adjacent to heat exchange layer 244 which contains heat exchange channels 246. The heat exchange channels 246 may be microchannels. A common wall 247 separates the process microchannel 242 from the heat exchange layer 244. The process microchannel 242 contains reaction zones 202 and 204. FIG. 10 indicates that the ratio of the length of first reaction zone 202 to length of the second or another reaction zone 204 is about 1:1. Alternatively, the ratio of the length of the first reaction zone 202 to the length of the second or another reaction zone 204 may be in the range from about 95:5 to about 5:95, and in one embodiment from about 90:10 to about 10:90, and in one embodiment from about 80:20 to about 20:80, and in one embodiment from about 70:30 to about 30:70. A catalyst is positioned in each of the reaction zones 202 and 204. The reactant composition (i.e., synthesis gas) flows through the reaction zones 202 and 204 in the direction indicated by arrows 260 and 262, contacts the catalyst in each reaction zone, and reacts to form the desired product. The desired product (i.e., methane, methanol and/or dimethyl ether) flows out of the process microchannel 242 as indicated by arrow 262. Heat exchange fluid flows through the heat exchange channels 246 in a direction that is crosscurrent to the flow of process fluid in the process microchannel 242. The reaction conducted in the process microchannel 242 is exothermic and the heat exchange fluid provides cooling for the reaction.

The average temperature in the first reaction zone 202 for the methanol or dimethyl ether synthesis reaction may be in the range from about 150° C. to about 400° C., and in one embodiment in the range from about 200° C. to about 350° C. The average temperature in the first reaction zone 202 for the methane synthesis reaction may be in the range from about 250° C. to about 850° C., and in one embodiment in the range from about 300° C. to about 700° C. The average temperature in the second or another reaction zone 204 may be at least about 5° C. less than the average temperature in first reaction zone 202, and in one embodiment the average temperature in second reaction zone 204 may be at least about 10° C. less than the average temperature in the first reaction zone 202, and in one embodiment the average temperature in second reaction zone 204 may be at least about 15° C. less than the average temperature in the first reaction zone 202, and in one embodiment the average temperature in second reaction zone 204 may be at least about 20° C. less than the average temperature in the first reaction zone 202, and in one embodiment the average temperature in second reaction zone 204 may be at least about 25° C. less than the average temperature in the first reaction zone 202, and in one embodiment the average temperature in second reaction zone 204 may be at least about 30° C. less than the average temperature in the first reaction zone 202, and in one embodiment the average temperature in second reaction zone 204 may be at least about 35° C. less than the average temperature in the first reaction zone 202, and in one embodiment the average temperature in second reaction zone 204 may be at least about 40° C. less than the average temperature in the first reaction zone 202, and in one embodiment the average temperature in second reaction zone 204 may be at least about 45° C. less than the average temperature in the first reaction zone 202, and in one embodiment the average temperature in second reaction zone 204 may be at least about 50° C. less than the average temperature in the first reaction zone 202, and in one embodiment the average temperature in second reaction zone 204 may be at least about 55° C. less than the average temperature in the first reaction zone 202, and in one embodiment the average temperature in second reaction zone 204 may be at least about 60° C. less than the average temperature in the first reaction zone 202. The average temperature in each reaction zone may be determined by taking the average of (1) the temperature at the inlet of the reaction zone, (2) the temperature at the midpoint along the axial length of the reaction zone, and (3) the temperature at the outlet of the reaction zone.

Figure 11:
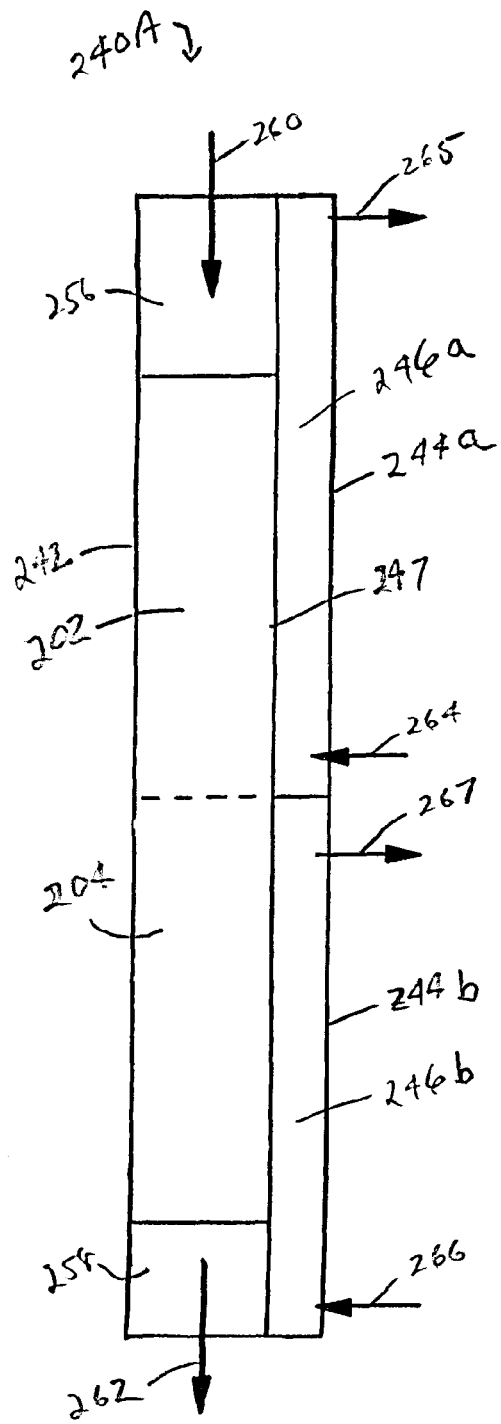

Alternatively, the process microchannel and heat exchange channels may be aligned as provided for in repeating unit 240A. Repeating unit 240A, which is illustrated in FIG. 11, is the same as the repeating unit 240 illustrated in FIG. 10 with the exception that the heat exchange channels 246a and 246b are rotated 90° and the heat exchange fluid flowing through the heat exchange channels flows in a direction that is countercurrent to the flow of process fluid in the process microchannel 242. Alternatively, the direction of flow of the heat exchange fluid may be co-current to the flow of process fluid in the process microchannel. The reaction zone 202 has an adjacent heat exchange zone 244a. Heat exchange fluid flows through the heat exchange zone 244a as indicated by arrows 264 and 265. The reaction zone 204 has an adjacent heat exchange zone 244b. Heat exchange fluid flows through the heat exchange zone 244b as indicated by arrows 266 and 267.

Figures 12, 13:
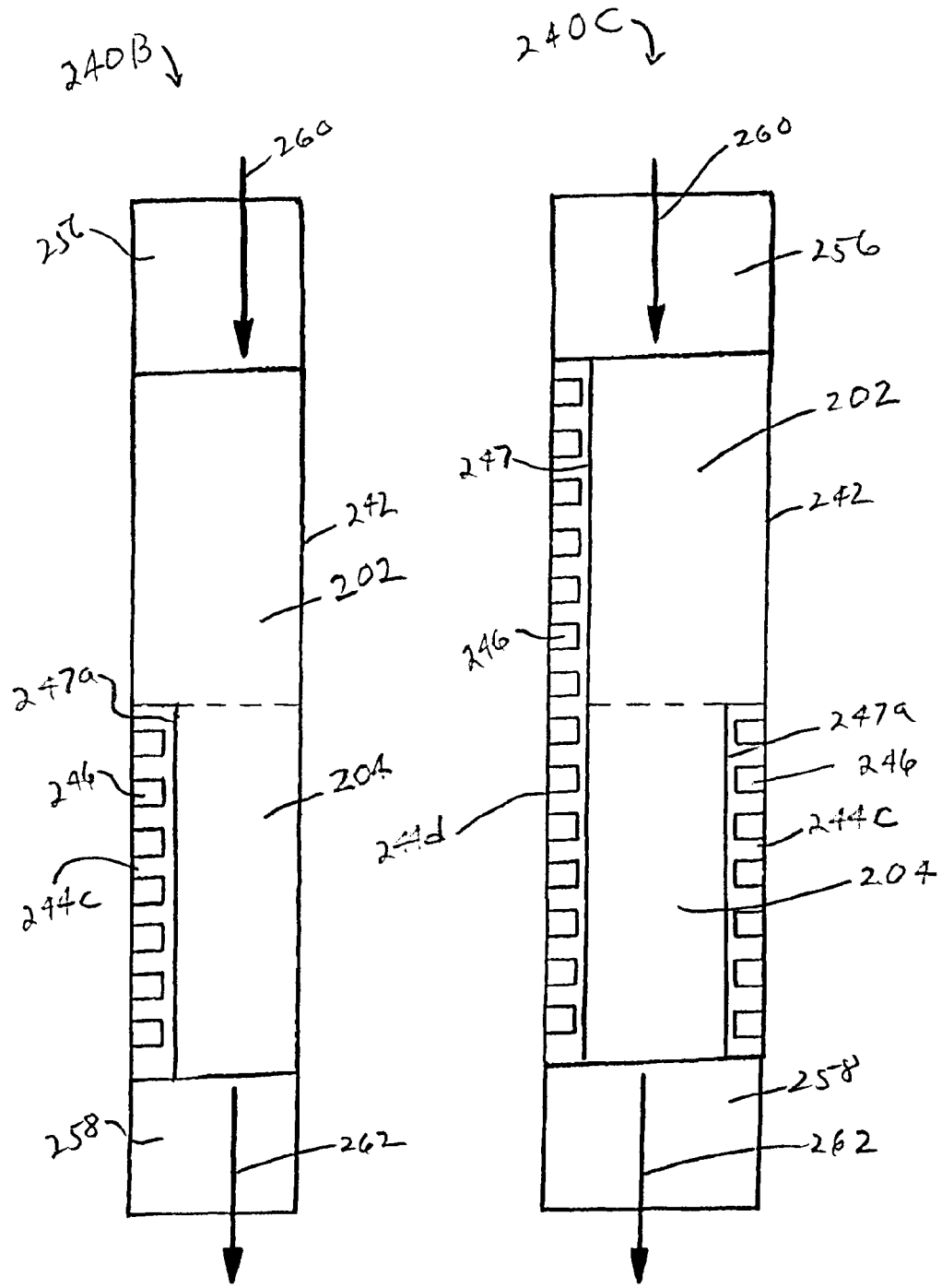

Alternatively, the process microchannels and heat exchange channels may be aligned as provided for in repeating unit 240B. Repeating unit 240B is illustrated in FIG. 12. Referring to FIG. 12, process microchannel 242 is positioned adjacent to heat exchange layer 244c. Common wall 247a separates the heat exchange layer 244c and the process microchannel 242. Heat exchange layer 244c contains a plurality of heat exchange channels 246 aligned in parallel relative to one another. Each heat exchange channel 246 extends lengthwise at a right angle relative to the lengthwise direction of the process microchannel 242. Heat exchange layer 244c is adjacent to reaction zone 204. There are no heat exchange channels adjacent to reaction zone 202. Thus, added cooling is provided for in the reaction zone 204, but not the reaction zone 202.

Alternatively, the process microchannels and heat exchange channels may be aligned as provided for in repeating unit 240C. Repeating unit 240C, which is illustrated in FIG. 13, is the same as repeating unit 240B illustrated in FIG. 12 with the exception that repeating unit 240C includes both heat exchange layers 244c and 244d. These heat exchange layers are positioned adjacent to and on opposite sides of the process microchannel 242. These heat exchange layers contain a plurality of parallel heat exchange channels 246. The heat exchange layer 244d provides cooling for the reaction zone 202. Both of the heat exchange layers 244c and 244d provide cooling for the reaction zone 204.

The process microchannels 242 may have a cross section having any shape, for example, a square, rectangle, circle, semi-circle, etc. The internal height of each process microchannel 242 may be considered to be the smaller of the internal dimensions normal to the direction of flow of reactants and product through the process microchannel. Each process microchannel 242 may have an internal height of up to about 10 mm, and in one embodiment up to about 6 mm, and in one embodiment up to about 4 mm, and in one embodiment up to about 2 mm. In one embodiment, the height may be in the range of about 0.05 to about 10 mm, and in one embodiment about 0.05 to about 6 mm, and in one embodiment about 0.05 to about 4 mm, and in one embodiment about 0.05 to about 2 mm. The width of each process microchannel 242 may be considered to be the other internal dimension normal to direction of flow of reactants and product through the process microchannel. The width of each process microchannel 242 may be of any dimension, for example, up to about 3 meters, and in one embodiment about 0.01 to about 3 meters, and in one embodiment about 0.1 to about 3 meters. The length of each process microchannel 242 may be of any dimension, for example, up to about 10 meters, and in one embodiment about 0.2 to about 10 meters, and in one embodiment from about 0.2 to about 6 meters, and in one embodiment from 0.2 to about 3 meters.

The heat exchange channels 246 may be microchannels or they may have dimensions that would classify them as not being microchannels. Each of the heat exchange channels 246 may have a cross section having any shape, for example, a square, rectangle, circle, semi-circle, etc. The internal height of each heat exchange channel 246 may be considered to be the smaller of the internal dimensions normal to the direction of flow of heat exchange fluid through the heat exchange channels. Each of the heat exchange channels 246 may have an internal height of up to about 2 mm, and in one embodiment in the range of about 0.05 to about 2 mm, and in one embodiment about 0.05 to about 1.5 mm. The width of each of these channels, which would be the other internal dimension normal to the direction of flow of heat exchange fluid through the heat exchange channel, may be of any dimension, for example, up to about 3 meters, and in one embodiment from about 0.01 to about 3 meters, and in one embodiment about 0.1 to about 3 meters. The length of each of the heat exchange channels 246 may be of any dimension, for example, up to about 10 meters, and in one embodiment from about 0.2 to about 10 meters, and in one embodiment from about 0.2 to about 6 meters, and in one embodiment from 0.2 to about 3 meters.

The number of repeating units 240-240C in the microchannel reactor 200 may be an desired number, for example, one, two, three, four, six, eight, ten, hundreds, thousands, tens of thousands, hundreds of thousands, millions, etc.

In the design and operation of the microchannel reactor 200 it may be advantageous to provide a tailored heat exchange profile along the length of the process microchannels 242 in order to optimize the reaction. This may be accomplished by matching the local release of heat given off by the exothermic reactions conducted in the process microchannels with heat removal or cooling provided by heat exchange fluid in the heat exchange channels 246 adjacent to and/or in thermal contact with the process microchannels. The extent of the reaction and the consequent heat release provided by the reaction may be higher in the front or upstream sections of the reaction zones 202 and 204 in the process microchannels as compared to the back or downstream sections of the reaction zones. Consequently, the matching cooling requirements may be higher in the upstream sections of the reaction zones as compared to the downstream sections of the reaction zones. Tailored heat exchange may be accomplished by providing more heat exchange or cooling channels 246, and consequently the flow of more heat exchange or cooling fluid, in thermal contact with upstream sections of the reaction zones 202 and 204 as compared to the downstream sections of the reaction zones. Heat transfer from the process microchannels to the heat exchange channels may be designed for optimum performance by selecting optimum heat exchange channel dimensions and/or the rate of flow of heat exchange fluid per individual or groups of heat exchange channels (i.e., heat exchange zones). Additional design alternatives for tailoring heat exchange may relate to the selection and design of the catalyst (such as, particle size, catalyst formulation, packing density, use of a graded catalyst, or other chemical or physical characteristics) at specific locations within the process microchannels. These design alternatives may impact both heat release from the process microchannels as well as heat transfer to the heat exchange fluid. Temperature differentials between the process microchannels and the heat exchange channels, which may provide the driving force for heat transfer, may be constant or may vary along the length of the process microchannels.

The process microchannels and heat exchange channels in the microchannel reactor 200 may have rectangular cross sections and may be aligned in side-by-side vertically oriented planes or horizontally oriented stacked planes. These planes may be tilted at an inclined angle from the horizontal. These configurations may be referred to as parallel plate configurations. These channels may be arranged in modularized compact units for scale-up.

The microchannel reactor 200 may be made of any material that provides sufficient strength, dimensional stability and heat transfer characteristics to permit operation of the inventive process. These materials may include aluminum; titanium; nickel; platinum; rhodium; copper; chromium; alloys of any of the foregoing metals; brass; steel (e.g., stainless steel); quartz; silicon; or a combination of two or more thereof. The microchannel reactor may be constructed of stainless steel with one or more copper or aluminum waveforms being used for forming the channels.

The microchannel reactor 200 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel reactor 200 may be constructed by forming shims with portions removed that allow flow passage. A stack of shims may be assembled via diffusion bonding, laser welding, diffusion brazing, and similar methods to form an integrated device. The microchannel reactors may be assembled using a combination of shims or laminae and partial sheets or strips. In this method, the channels or void areas may be formed by assembling strips or partial sheets to reduce the amount of material required.

The microchannel reactor 200 may be constructed using waveforms in the form of right angled corrugated inserts. These inserts may be sandwiched between opposing planar sheets or shims. In this manner the microchannels may be defined on three sides by the corrugated insert and on the fourth side by one of the planar sheets or shims. The process microchannels as well as the heat exchange channels may be formed in this manner. Microchannel reactors made using waveforms are disclosed in WO 2008/030467, which is incorporated herein by reference.

The process microchannels and/or heat exchange channels may contain one or more surface features in the form of depressions in and/or projections from one or more interior walls of the process microchannels and/or heat exchange channels. Examples of surface feature designs that may be used are shown in FIGS. 20 and 21. The surface features may be used to disrupt the flow of fluid flowing in the channels. These disruptions in flow may enhance mixing and/or heat transfer. The surface features may be in the form of patterned surfaces. The microchannel reactor 200 may be made by laminating a plurality of shims together. One or both major surfaces of the shims may contain surface features. Alternatively, the microchannel reactor 200 may be assembled using some sheets or shims and some strips, or partial sheets to reduce the total amount of metal required to construct the device. In one embodiment, a shim containing surface features may be paired (on opposite sides of a microchannel) with another shim containing surface features. Pairing may create better mixing or heat transfer enhancement as compared to channels with surface features on only one major surface. In one embodiment, the patterning may comprise diagonal recesses that are disposed over substantially the entire width of a microchannel surface. The patterned surface feature area of a wall may occupy part of or the entire length of a microchannel surface. In one embodiment, surface features may be positioned over at least about 10%, and in one embodiment at least about 20%, and in one embodiment at least about 50%, and in one embodiment at least about 80% of the length of a channel surface. Each diagonal recesses may comprise one or more angles relative to the flow direction. Successive recessed surface features may comprise similar or alternate angles relative to other recessed surface features.

In embodiments wherein surface features may be positioned on or in more than one microchannel wall, the surface features on or in one wall may have the same (or similar) pattern as found on a second wall, but rotated about the centerline of the main channel mean bulk flow direction. In embodiments wherein surface features may be on or in opposite walls, the surface features on or in one wall may be approximately mirror images of the features on the opposite wall. In embodiments wherein surface features are on or in more than one wall, the surface features on or in one wall may be the same (or similar) pattern as found on a second wall, but rotated about an axis which is orthogonal to the main channel mean bulk flow direction. In other words, the surface features may be flipped 180 degrees relative to the main channel mean bulk flow direction and rotated about the centerline of the main channel mean bulk flow. The surface features on or in opposing or adjacent walls may or may not be aligned directly with one another, but may be repeated continuously along the wall for at least part of the length of the wall. Surface features may be positioned on three or more interior surfaces of a channel. For the case of channel geometries with three or fewer sides, such as triangular, oval, elliptical, circular, and the like, the surface features may cover from about 20% to about 100% of the perimeter of the microchannel.

A patterned surface may comprise multiple patterns stacked on top of each other. A pattern or array of holes may be placed adjacent to a heat transfer wall and a second pattern, such as a diagonal array of surface features may be stacked on top and adjacent to an open channel for flow. A sheet adjacent to an open gap may have patterning through the thickness of the sheet such that flow may pass through the sheet into an underlying pattern. Flow may occur as a result of advection or diffusion. As an example, a first sheet with an array of through holes may be placed over a heat transfer wall, and a second sheet with an array of diagonal through slots may be positioned on the first sheet. This may create more surface area for adhering a catalyst. In one embodiment, the pattern may be repeated on at least one other wall of the process microchannel. The patterns may be offset on opposing walls. The innermost patterned surfaces (those surfaces bounding a flow channel) may contain a pattern such as a diagonal array. The diagonal arrays may be oriented both "with" the direction of flow or one side oriented with the direction of flow and the opposing side oriented "against" the direction of flow. By varying surface features on opposing walls, different flow fields and degrees of vorticity may be created in the fluid that travels down the center and open gap.

The surface features may be oriented at angles relative to the direction of flow through the channels. The surface features may be aligned at an angle from about 1° to about 89°, and in one embodiment from about 30° to about 75°, relative to the direction of flow. The angle of orientation may be an oblique angle. The angled surface features may be aligned toward the direction of flow or against the direction of flow. The flow of fluid in contact with the surface features may force some of the fluid into depressions in the surface features, while other fluids may flow above the surface features. Flow within the surface features may conform with the surface feature and be at an angle to the direction of the bulk flow in the channel. As fluid exits the surface features it may exert momentum in the x and y direction for an x,y,z coordinate system wherein the bulk flow is in the z direction. This may result in a churning or rotation in the flow of the fluids. This pattern may be helpful for mixing.

Two or more surface feature regions within the process microchannels may be placed in series such that mixing of the fluids may be accomplished using a first surface feature region, followed by at least one second surface feature region where a different flow pattern may be used.

The surface features may have two or more layers stacked on top of each other or intertwined in a three-dimensional pattern. The pattern in each discrete layer may be the same or different. Flow may rotate or advect in each layer or only in one layer. Sub-layers, which may not be adjacent to the bulk flow path of the channel, may be used to create additional surface area. The flow may rotate in the first level of surface features and diffuse molecularly into the second or more sublayers to promote reaction. Three-dimensional surface features may be made via metal casting, photochemical machining, laser cutting, etching, ablation, or other processes where varying patterns may be broken into discrete planes as if stacked on top of one another. Three-dimensional surface features may be provided adjacent to the bulk flow path within the microchannel where the surface features have different depths, shapes, and/or locations accompanied by sub-features with patterns of varying depths, shapes and/or locations.

An example of a three-dimensional surface feature structure may comprise recessed oblique angles or chevrons at the interface adjacent the bulk flow path of the microchannel. Beneath the chevrons there may be a series of three-dimensional structures that connect to the surface features adjacent to the bulk flow path but are made from structures of assorted shapes, depths, and/or locations. It may be further advantageous to provide sublayer passages that do not directly fall beneath an open surface feature that is adjacent to the bulk flow path within the microchannel but rather connect through one or more tortuous two-dimensional or three-dimensional passages. This approach may be advantageous for creating tailored residence time distributions in the microchannels, where it may be desirable to have a wider versus more narrow residence time distribution.

The length and width of a surface feature may be defined in the same way as the length and width of a channel. The depth may be the distance which the surface feature sinks into or rises above the microchannel surface. The depth of the surface features may correspond to the direction of stacking a stacked and bonded microchannel device with surface features formed on or in the sheet surfaces. The dimensions for the surface features may refer the maximum dimension of a surface feature; for example the depth of a rounded groove may refer to the maximum depth, that is, the depth at the bottom of the groove.

The surface features may have depths that are up to about 5 mm, and in one embodiment up to about 2 mm, and in one embodiment in the range from about 0.01 to about 5 mm, and in one embodiment in the range from about 0.01 to about 2 mm, and in one embodiment in the range from about 0.01 mm to about 1 mm. The width of the surface features may be sufficient to nearly span the microchannel width (for example, herringbone designs), but in one embodiment (such as fill features) may span about 60% or less of the width of the microchannel, and in one embodiment about 50% or less, and in one embodiment about 40% or less, and in one embodiment from about 0.1% to about 60% of the microchannel width, and in one embodiment from about 0.1% to about 50% of the microchannel width, and in one embodiment from about 0.1% to about 40% of the microchannel width. The width of the surface features may be in the range from about 0.05 mm to about 100 cm, and in one embodiment in the range from about 0.5 mm to about 5 cm, and in one embodiment in the range from about 1 to about 2 cm.

Multiple surface features or regions of surface features may be included within a channel, including surface features that recess at different depths into one or more microchannel walls. The spacing between recesses may be in the range from about 0.01 mm to about 10 mm, and in one embodiment in the range from about 0.1 to about 1 mm. The surface features may be present throughout the entire length of a microchannel or in portions or regions of the channel. The portion or region having surface features may be intermittent so as to promote a desired mixing or unit operation (for example, separation, cooling, etc.) in tailored zones. For example, a one-centimeter section of a channel may have a tightly spaced array of surface features, followed by four centimeters of a flat channel without surface features, followed by a two-centimeter section of loosely spaced surface features. The term "loosely spaced surface features" may be used to refer to surface features with a pitch or feature to feature distance that is more than about five times the width of the surface feature.

The surface features may be positioned in one or more surface feature regions that extend substantially over the entire axial length of a channel. In one embodiment, a channel may have surface features extending over about 50% or less of its axial length, and in one embodiment over about 20% or less of its axial length. In one embodiment, the surface features may extend over about 10% to about 100% of the axial length of the channel, and in one embodiment from about 20% to about 90%, and in one embodiment from about 30% to about 80%, and in one embodiment from about 40% to about 60% of the axial length of a channel.

Each surface feature leg may be at an oblique angle relative to the bulk flow direction. The feature span length or span may be defined as being normal to the feature orientation. As an example, one surface feature may be a diagonal depression at a 45 degree angle relative to a plane orthogonal to the mean direction of bulk flow in the main channel with a 0.38 mm opening or span or feature span length and a feature run length of 5.6 mm. The run length may be the distance from one end to the other end of the surface feature in the longest direction, whereas the span or feature span length may be in the shortest direction (that is not depth). The surface feature depth may be the distance way from the main channel. For surface features with a nonuniform width (span), the span may be the average span averaged over the run length.

A surface feature may comprise a recess or a protrusion based on the projected area at the base of the surface feature or the top of the surface feature. If the area at the top of the surface feature is the same or exceeds the area at the base of the surface feature, then the surface feature may be considered to be recessed. If the area at the base of the surface feature exceeds the area at the top of the surface feature, then it may be considered to be protruded. For this description, the surface features may be described as recessed although it is to be understood that by changing the aspect ratio of the surface feature it may be alternatively defined as a protrusion. For a process microchannel defined by walls that intersect only the tops of the surface features, especially for a flat channel, all surface features may be defined as recessed and it is to be understood that a similar channel could be created by protruding surface features from the base of a channel with a cross section that includes the base of the surface features.

The process microchannels and/or heat exchange channels may have at least about 20%, and in one embodiment at least about 35%, and in one embodiment at least about 50%, and in one embodiment at least about 70%, and in one embodiment at least about 90% of the interior surface of the channel (measured in cross-section perpendicular to length; i.e., perpendicular to the direction of net flow through the channel) that contains surface features. The surface features may cover a continuous stretch of at least about 1 cm, and in one embodiment at least about 5 cm. In the case of an enclosed channel, the percentage of surface feature coverage may be the portion of a cross-section covered with surface features as compared to an enclosed channel that extends uniformly from either the base or the top of the surface feature or a constant value in-between. The latter may be a flat channel. For example, if a channel has patterned top and bottom surfaces that are each 0.9 cm across (wide) and unpatterned side walls that are 0.1 cm high, then 90% of the surface of the channel would contain surface features.

The process microchannels may be enclosed on all sides, and in one embodiment the channel may have a generally square or rectangular cross-section (in the case of rectangular channel, surface feature patterning may be positioned on both major faces). For a generally square or rectangular channel, the channel may be enclosed on only two or three sides and only the two or three walled sides may be used in the above described calculation of percentage surface features. In one embodiment, the surface features may be positioned on cylindrical channels with either constant or varying cross section in the axial direction.

Each of the surface feature patterns may be repeated along one face of the channel, with variable or regular spacing between the surface features in the channel bulk flow direction. Some embodiments may have only a single leg to each surface feature, while other embodiments may have multiple legs (two, three, or more). For a wide-width channel, multiple surface features or columns of repeated surface features may be placed adjacent to one another across the width of the channel. For each of the surface feature patterns, the feature depth, width, span, and spacing may be variable or constant as the pattern is repeated along the bulk flow direction in the main channel. Also, surface feature geometries having an apex connecting two legs at different angles may have alternate embodiments in which the surface feature legs may not be connected at the apex.

The catalyst for the methanol and dimethyl ether reactions may comprise any catalyst suitable for synthesizing methanol or dimethyl ether from synthesis gas. These may include catalysts comprising copper, zinc and aluminum oxides (e.g., gamma-alumina), and optionally further containing, for example, oxides of one or more rare earth elements (i.e., elements 57-71), zirconium, yttrium, chromium, silver, gallium, vanadium, molybdenum, tungsten or titanium. The ranges of proportions may be from about 30 to about 70% by weight as copper, from about 20 to about 70% by weight as zinc, and up to about 15% by weight as aluminum. Examples of methanol synthesis catalysts that may be used may include those disclosed in U.S. Pat. Nos. 4,596,782; 5,238,895; 5,254,520; 5,384,335; 5,610,202; 5,767,039; 6,114,279; 6,342,538 B1; 6,433,029 B1; and 6,486,219 B1; and U.S. Patent Publication 2002/0177741 A1.

The dimethyl ether catalysts that may be used may include those disclosed in U.S. Pat. Nos. 4,011,275; 6,069, 180; 6,147,125; 6,248,795; 6,638,892; and J. L. Dubois et al., "Conversion of Carbon Dioxide to Dimethyl Ether and Methanol Over Hybrid Catalysts," Chem. Lett., (7) 1115-1118 (1992). These patents and publications are incorporated herein by reference.

The alcohol forming catalyst may be used in combination with a dehydration catalyst to provide a synthesis-gas-to-dimethylether route. Examples of the dehydration catalyst that may be used include acidic oxides such as alumina, silica-alumina, zeolite, and silico-alumino-phosphate synthetic molecular sieves. These are disclosed in U.S. 2006/0020155A1 and US 2007/0244000A1, which are incorporated herein by reference. The alcohol forming catalyst and the dehydration catalyst may be mixed or combined together in the same reaction zone. Alternatively, the dehydration catalyst may be positioned downstream of the alcohol forming catalyst, either in the same microchannel reactor or in a separate microchannel reactor.

The catalyst used for the methane forming reactions may comprise any catalyst suitable for converting synthesis gas to methane. The catalyst may comprise nickel, iron, cobalt, ruthenium, molybdenum, vanadium, titanium, or a mixture of two or more thereof. The catalyst may comprise an oxide of any of the foregoing metals. The catalyst may comprise vanadium and/or molybdenum in the form of free metal, salt, oxide and/or sulfide on a porous, oxidic support comprising titanium dioxide. The catalyst may be promoted with one or more salts, hydroxides, oxides or sulfides of one or more metals belonging to Groups IA, IIA or IIIB of the Periodic Table. The catalyst may comprise vanadium sulfide promoted with cerium sulfide on a porous support comprising titanium dioxide. The catalysts that may be used are described in U.S. Pat. No. 4,540,714, which is incorporated herein by reference.

The catalyst may be positioned in each of the reaction zones 202 and 204 in the process microchannels. The same or different catalyst may be used in each reaction zone. The catalyst may be a graded catalyst. In each reaction zone the length of one or more heat exchange zone(s) adjacent to or in thermal contact with the reaction zone may vary in their dimensions. For example, in one embodiment, the length of the one or more of these heat exchange zones may be less than about 50% of the length of each reaction zone. Alternatively, the one or more heat exchange zones may have lengths that are more than about 50% of the length of each reaction zone up to about 100% of the length of each reaction zone.

The catalyst may have any size and geometric configuration that fits within the process microchannels. The catalyst may be in the form of particulate solids (e.g., pellets, powder, fibers, and the like) having a median particle diameter of about 1 to about 1000 µm (microns), and in one embodiment about 10 to about 500 µm, and in one embodiment about 25 to about 250 µm. In one embodiment, the catalyst is in the form of a fixed bed of particulate solids.

Figure 14:
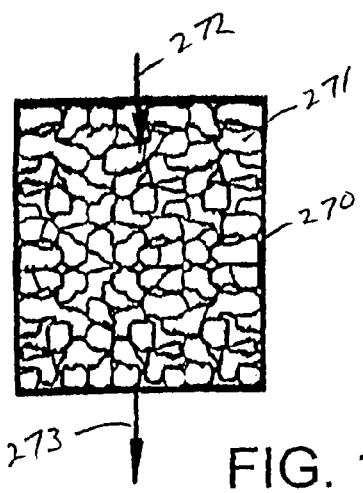
FIGS. 14-19 are schematic illustrations of catalysts or catalyst supports that may be used in the process microchannels used in the microchannel reactor. The catalyst illustrated in FIG. 14 is in the form of a bed of particulate solids. The catalyst illustrated in FIG. 15 has a flow-by design. The catalyst illustrated in FIG. 16 is a flow-through structure.

In one embodiment, the catalyst may be in the form of a fixed bed of particulate solids (as shown in FIG. 14). The median particle diameter of the particulate solids may be small, and the length of each process microchannel may be relatively short. The median particle diameter may be in the range of about 1 to about 1000 µm, and in one embodiment about 10 to about 500 µm, and the length of each process microchannel may be in the range of up to about 1000 cm, and in one embodiment about 10 to about 500 cm, and in one embodiment about 50 to about 300 cm.

Referring to FIG. 14, the catalyst 271, which is in the form of a bed of particulate solids, is contained in process microchannel 270. Reactants enter the fixed bed as indicated by arrow 272, undergo reaction, and product flows out of the fixed bed as indicated by arrow 273.

The catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The catalyst may be supported on a honeycomb structure. The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow.

Figure 15:
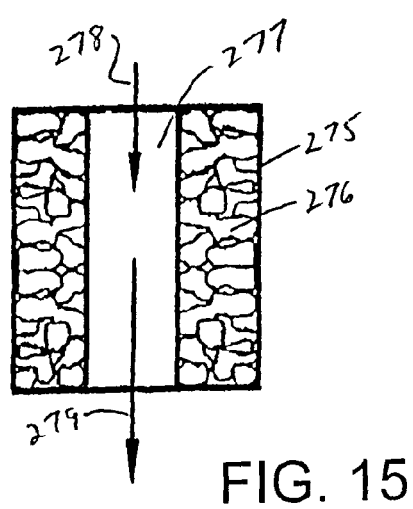

An example of a flow-by structure is illustrated in FIG. 15. In FIG. 15, the catalyst 276 is contained within process microchannel 275. An open passage way 277 permits the flow of fluid through the process microchannel 275 as indicated by arrows 278 and 272. The reactants contact the catalyst and undergo reaction to form product.

Figure 16:
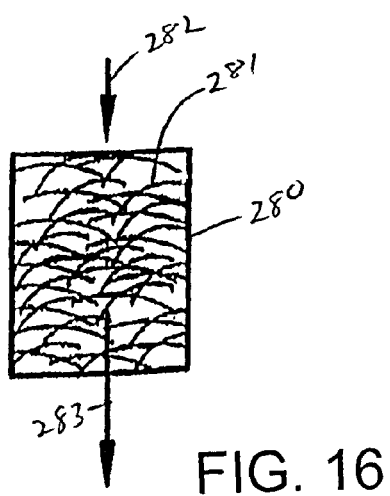

The catalyst may be supported on a flow-through support structure such as a foam, wad, pellet, powder, or gauze. An example of a flow-through structure is illustrated in FIG. 16. In FIG. 16, the flow-through catalyst 281 is contained within process microchannel 280, the reactants flow through the catalyst 281 as indicated by arrows 282 and 283, and undergo reaction to form the product.

The support structure for a flow-through catalyst may be formed from a material comprising silica gel, foamed copper, sintered stainless steel fiber, steel wool, alumina, or a combination of two or more thereof. In one embodiment, the support structure may be made of a heat conducting material, such as a metal, to enhance the transfer of heat to or from the catalyst.

The catalyst may be directly washcoated on the interior walls of the process microchannels or combustion channels, grown on the channel walls from solution, or coated on a fin structure. The catalyst may be in the form of a single piece of porous contiguous material, or many pieces in physical contact. In one embodiment, the catalyst may comprise a contiguous material and have a contiguous porosity such that molecules can diffuse through the catalyst. In this embodiment, the fluids flow through the catalyst rather than around it. In one embodiment, the cross-sectional area of the catalyst may occupy from about 1 to about 99%, and in one embodiment about 10 to about 95% of the cross-sectional area of the process microchannels and/or combustion channels. The catalyst may have a surface area, as measured by BET, of greater than about 0.5 $m^2/g$, and in one embodiment greater than about 2 $m^2/g$.

The catalyst may comprise a porous support, an interfacial layer on the porous support, and a catalyst material on the interfacial layer. The interfacial layer may be solution deposited on the support or it may be deposited by chemical vapor deposition or physical vapor deposition. In one embodiment the catalyst has a porous support, a buffer layer, an interfacial layer, and a catalyst material. Any of the foregoing layers may be continuous or discontinuous as in the form of spots or dots, or in the form of a layer with gaps or holes. The porous support may have a porosity of at least about 5% as measured by mercury porosimetry and an average pore size (sum of pore diameters divided by number of pores) of about 1 to about 1000 microns. The porous support may be a porous ceramic or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may comprise $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may comprise a metal oxide. Examples of metal oxides that may be used include $\alpha$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. The interfacial layer may be used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 μm, and in one embodiment from about 1 to about 50 microns. The interfacial layer may be either crystalline or amorphous. The interfacial layer may have a BET surface area of at least about 1 $m^2/g$.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

Figure 17:
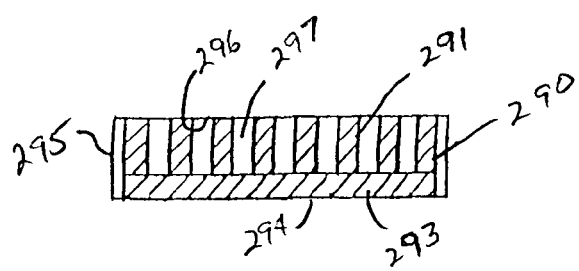
Figure 18:
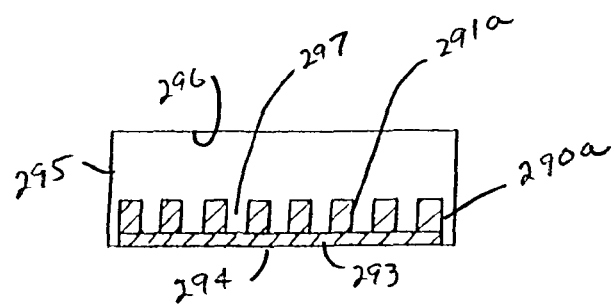
Figure 19:
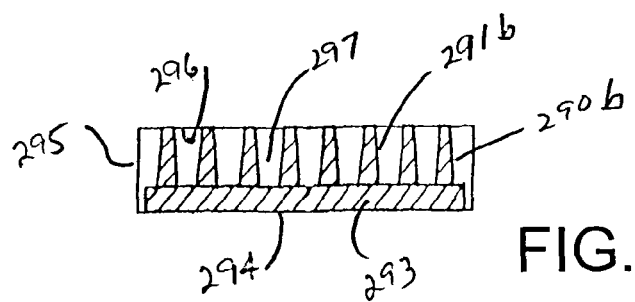

The catalyst may be supported on an assembly of one or more fins positioned within the process microchannels. Examples are illustrated in FIGS. 17-19. Referring to FIG. 17, fin assembly 290 includes fins 291 which are mounted on fin support 293 which overlies base wall 294 of process microchannel 295. The fins 291 project from the fin support 293 into the interior of the process microchannel 295. The fins 291 may extend to and contact the interior surface of upper wall 296 of process microchannel 295. Fin channels 297 between the fins 291 provide passage ways for reactant and product to flow through the process microchannel 295 parallel to its length. Each of the fins 291 has an exterior surface on each of its sides. The exterior surface provides a support base for the catalyst. The reactants may flow through the fin channels 297, contact the catalyst supported on the exterior surface of the fins 291, and react to form product. The fin assembly 290*a* illustrated in FIG. 18 is similar to the fin assembly 290 illustrated in FIG. 17 except that the fins 291*a* do not extend all the way to the interior surface of the upper wall 296 of the microchannel 295. The fin assembly 290b illustrated in FIG. 19 is similar to the fin assembly 290 illustrated in FIG. 17 except that the fins 291b in the fin assembly 290b have cross sectional shapes in the form of trapezoids. Each of the fins may have a height ranging from about 0.02 mm up to the height of the process microchannel 285, and in one embodiment from about 0.02 to about 10 mm, and in one embodiment from about 0.02 to about 5 mm, and in one embodiment from about 0.02 to about 2 mm. The width of each fin may range from about 0.02 to about 5 mm, and in one embodiment from about 0.02 to about 2 mm and in one embodiment about 0.02 to about 1 mm. The length of each fin may be of any length up to the length of the process microchannel 295, and in one embodiment up to about 10 m, and in one embodiment about 0.5 to about 10 m, and in one embodiment about 0.5 to about 6 m, and in one embodiment about 0.5 to about 3 m. The gap between each of the fins may be of any value and may range from about 0.02 to about 5 mm, and in one embodiment from about 0.02 to about 2 mm, and in one embodiment from about 0.02 to about 1 mm. The number of fins in the process microchannel 295 may range from about 1 to about 50 fins per centimeter of width of the process microchannel 295, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. Each of the fins may have a cross-section in the form of a rectangle or square as illustrated in FIG. 17 or 18, or a trapezoid as illustrated in FIG. 19. When viewed along its length, each fin may be straight, tapered or have a serpentine configuration. The fin assembly may be made of any material that provides sufficient strength, dimensional stability and heat transfer characteristics to permit operation for which the process microchannel is intended. These materials include: steel (e.g., stainless steel, carbon steel, and the like); aluminum; titanium; nickel; platinum; rhodium; copper; chromium; alloys of any of the foregoing metals; monel; inconel; brass; polymers (e.g., thermoset resins); ceramics; glass; quartz; silicon; or a combination of two or more thereof. The fin assembly may be made of an $Al_2O_3$ or a $Cr_2O_3$ forming material. The fin assembly may be made of an alloy comprising Fe, Cr, Al and Y, or an alloy comprising Ni, Cr and Fe.

The catalyst may be in the form of a bed of particulates which may be graded in composition or graded with a thermally conductive inert material. The thermally conductive inert material may be interspersed with the active catalyst. Examples of thermally conductive inert materials that may be used include diamond powder, silicon carbide, aluminum, alumina, copper, graphite, and the like. The catalyst bed fraction may range from about 100% by weight active catalyst to less than about 50% by weight active catalyst. The catalyst bed fraction may range from about 10% to about 90% by weight active catalyst, and in one embodiment from about 25% to about 75% by weight. In an alternate embodiment the thermally conductive inert material may be deployed at the center of the catalyst or within the catalyst particles. The active catalyst may be deposited on the outside, inside or intermittent within a composite structure that includes the thermally conductive inert. The resultant catalyst composite structure may have an effective thermal conductivity when placed in a process microchannel or combustion channel that is at least about 0.3 W/m/K, and in one embodiment at least about 1 W/m/K, and in one embodiment at least about 2 W/m/K.

The catalyst may be graded locally within the process microchannel. For example, a process microchannel may contain a catalyst bed with the first reaction zone 202 and the second reaction zone 204. The top or bottom (or front or back) of the catalyst bed may be graded in composition whereby a more or less active catalyst is employed in all or part of the first or second reaction zone. The composition that is reduced in one reaction zone may generate less heat per unit volume and thus reduce the hot spot and potential for the production of undesirable by-products. The catalyst may be graded with an inert material in the first and/or second reaction zone, in full or in part. The first reaction zone may contain a first composition of catalyst or inert material, while the second reaction zone may contain a second composition of catalyst or inert material.

Different particle sizes may be used in different axial regions of the process microchannels to provide for graded catalyst beds. For example, small particles may be used in the first reaction zone 202 while larger particles may be used in the second reaction zone 204, or vice versa. The average particle diameters may be less than half the height or gap of the process microchannels. The small particles may be less than one-fourth of the process microchannel height or gap. Larger particles may cause lower pressure drops per unit length of the process microchannels and may also reduce the catalyst effectiveness. The effective thermal conductivity of a catalyst bed may be lower for larger size particles. Smaller particles may be used in regions where improved heat transfer is sought throughout the catalyst bed or alternatively larger particles may be used to reduce the local rate of heat generation.

Relatively short contact times, high selectivity to the desired product and relatively low rates of deactivation of the catalyst may be achieved by limiting the diffusion path required for the catalyst. This may be achieved when the catalyst is in the form of a thin layer on an engineered support such as a metallic foam or on the wall of the process microchannel. This may allow for increased space velocities. The thin layer of catalyst may be produced using chemical vapor deposition. This thin layer may have a thickness in the range up to about 1 micron, and in one embodiment in the range from about 0.1 to about 1 micron, and in one embodiment in the range from about 0.1 to about 0.5 micron, and in one embodiment about 0.25 micron. These thin layers may reduce the time the reactants are within the active catalyst structure by reducing the diffusional path. This may decrease the time the reactants spend in the active portion of the catalyst. The result may be increased selectivity to the product and reduced unwanted by-products. An advantage of this mode of catalyst deployment may be that, unlike conventional catalysts in which the active portion of the catalyst may be bound up in an inert low thermal conductivity binder, the active catalyst film may be in intimate contact with either an engineered structure or a wall of the process microchannel. This may leverage high heat transfer rates attainable in the microchannel reactor and allow for close control of temperature. This may result in the ability to operate at increased temperature (faster kinetics) without promoting the formation of undesired by-products, thus producing higher productivity and yield and prolonging catalyst life.

The configuration of the microchannel reactor 200 may be tailored to match the reaction kinetics. Near the entrance or top of the first reaction zone 202 of a process microchannel, the microchannel height or gap may be smaller than in the second reaction zone 204 near the exit or bottom of the process microchannel. Alternatively, the reaction zones may be smaller than half the process microchannel length. For example, a first process microchannel height or gap may be used for the first 10%, 25%, 50%, 75%, or 90% of the length of the process microchannel for the first reaction zone 202, while a larger second height or gap may be used in the second reaction zone 204 downstream from the first reaction zone. Other gradations in the process microchannel height or gap may be used. For example, a first height or gap may be used near the entrance of the microchannel to provide the first reaction zone 202, a second height or gap downstream from the first reaction zone may be used to provide the additional reaction zone 220, and a third height or gap may be used to provide the second or another reaction zone 204 near the exit of the microchannel. The first and third heights or gaps may be the same or different. The first and third heights or gaps may be larger or smaller than the second height or gap. The third height or gap may be smaller or larger than the second height or gap. The second height or gap may be larger or smaller than the third height or gap.

In one embodiment, the catalyst may be regenerated by flowing a regenerating fluid through the process microchannels in contact with the catalyst. The regenerating fluid may comprise hydrogen or a diluted hydrogen stream. The diluent may comprise nitrogen, argon, helium, methane, carbon dioxide, steam, or a mixture of two or more thereof. The temperature of the regenerating fluid may be from about 50 to about 400° C., and in one embodiment about 200 to about 350° C. The pressure within the channels during this regeneration step may range from about 1 to about 40 atmospheres, and in one embodiment about 1 to about 20 atmospheres, and in one embodiment about 1 to about 5 atmospheres. The residence time for the regenerating fluid in the channels may range from about 0.01 to about 1000 seconds, and in one embodiment about 0.1 second to about 100 seconds.

The process microchannels may be characterized by having bulk flow paths. The term "bulk flow path" refers to an open path (contiguous bulk flow region) within the process microchannels or combustion channel. A contiguous bulk flow region allows rapid fluid flow through the channels without large pressure drops. In one embodiment, the flow of fluid in the bulk flow region is laminar. Bulk flow regions within each process microchannel or combustion channel may have a cross-sectional area of about 0.05 to about 10,000 mm$^2$, and in one embodiment about 0.05 to about 5000 mm$^2$, and in one embodiment about 0.1 to about 2500 mm$^2$. The bulk flow regions may comprise from about 5% to about 95%, and in one embodiment about 30% to about 80% of the cross-section of the process microchannels or combustion channel.

The overall contact time (that is, the combined contact time in the reaction zone 202 and 204, and optionally 220) of the reactants with the catalyst may range up to about 2000 milliseconds (ms), and in the range from about 10 to about 2000 ms, and in one embodiment from about 10 ms to about 1000 ms, and in one embodiment about 20 ms to about 500 ms. The contact time may range up to about 300 ms, and in one embodiment from about 20 to about 300 ms, and in one embodiment from about 50 to about 150 ms, and in one embodiment about 75 to about 125 ms, and in one embodiment about 100 ms. The contact time may be up to about 100 ms, and in one embodiment from about 10 to about 100 ms.

The space velocity (or gas hourly space velocity (GHSV)) for the flow of fluid in the process microchannels may be at least about 1000 hr$^{-1}$ (normal liters of feed/hour/liter of volume within the process microchannels). The space velocity may range from about 1000 to about 1,000,000 hr$^{-1}$, and in one embodiment in the range from about 10,000 to about 100,000 hr$^1$.

The pressure within the process microchannels may be up to about 50 atmospheres, and in one embodiment in the range from about 1 to about 50 atmospheres, and in one embodiment from about 2 to about 40 atmospheres, and in one embodiment from about 2 to about 10 atmospheres, and in one embodiment from about 10 to about 50 atmospheres, and in one embodiment from about 20 to about 30 atmospheres.

The pressure drop of fluids as they flow in the process microchannels may range up to about 10 atmospheres per meter of length of channel (atm/m), and in one embodiment up to about 5 atm/m, and in one embodiment up to about 3 atm/m.

The Reynolds Number for the flow of fluid in the process microchannels may be in the range of about 10 to about 4000, and in one embodiment about 100 to about 2000.

The heat exchange fluid entering the heat exchange channels of the microchannel reactor 200 may be at a temperature of about 100° C. to about 400° C., and in one embodiment about 200° C. to about 300° C. The heat exchange fluid exiting the heat exchange channels may be at a temperature in the range of about 150° C. to about 450° C., and in one embodiment about 200° C. to about 350° C. The residence time of the heat exchange fluid in the heat exchange channels may range from about 1 to about 2000 ms, and in one embodiment about 10 to about 500 ms. The pressure drop for the heat exchange fluid as it flows through the heat exchange channels may range up to about 10 atm/m, and in one embodiment from about 1 to about 10 atm/m, and in one embodiment from about 2 to about 5 atm/m. The heat exchange fluid may be in the form of a vapor, a liquid, or a mixture of vapor and liquid. The Reynolds Number for the flow of the heat exchange fluid in heat exchange channels may be from about 10 to about 4000, and in one embodiment about 100 to about 2000.

The heat exchange fluid used in the heat exchange channels may be any heat exchange fluid suitable for cooling an exothermic reaction. These may include air, steam, liquid water, gaseous nitrogen, other gases including inert gases, carbon monoxide, oils such as mineral oil, and heat exchange fluids such as Dowtherm A and Therminol which are available from Dow-Union Carbide.

The heat exchange channels used in microchannel reactor 200 may comprise process channels wherein an endothermic process is conducted. These heat exchange process channels may be microchannels. Examples of endothermic processes that may be conducted in the heat exchange channels include steam reforming and dehydrogenation reactions. Steam reforming of an alcohol that occurs at a temperature in the range from about 200° C. to about 300° C. is an example of an endothermic process that may be used. The incorporation of a simultaneous endothermic reaction to provide an improved heat sink may enable a typical heat flux of roughly an order of magnitude above the convective cooling heat flux.

The heat exchange fluid may undergo a partial or full phase change as it flows in the heat exchange channels of the microchannel reactor 200. This phase change may provide additional heat removal from the process microchannels beyond that provided by convective cooling. For a liquid heat exchange fluid being vaporized, the additional heat being transferred from the process microchannels may result from the latent heat of vaporization required by the heat exchange fluid. In one embodiment, about 50% by weight of the heat exchange fluid may be vaporized, and in one embodiment about 35% by weight may be vaporized, and in one embodiment about 20% by weight may be vaporized, and in one embodiment about 10% by weight may be vaporized. In one embodiment, from about 10% to about 50% by weight may be vaporized.

The heat flux for heat exchange in the microchannel reactor 200 may be in the range from about 0.01 to about 500 watts per square centimeter of surface area of the one or more heat transfer walls of the process microchannels (W/cm$^2$) in the microchannel reactor, and in one embodiment in the range from about 0.1 to about 250 W/cm$^2$, and in one embodiment from about 1 to about 25 W/cm$^2$, and in one embodiment, from about 1 to about 100 W/cm$^2$, and in one embodiment from about 1 to about 50 W/cm$^2$, and in one embodiment from about 1 to about 25 W/cm$^2$, and in one embodiment from about 1 to about 10 W/cm$^2$.

The control of heat exchange during the reaction process, in one embodiment, may be advantageous for controlling selectivity towards the desired product due to the fact that such added cooling may reduce or eliminate the formation of undesired by-products from undesired parallel reactions with higher activation energies.

The pressure within each individual heat exchange channel in the microchannel reactor 200 may be controlled using passive structures (e.g., obstructions), orifices and/or mechanisms upstream of the heat exchange channels or in the channels. By controlling the pressure within each heat exchange microchannel, the temperature within each heat exchange microchannel may be controlled. A higher inlet pressure for each heat exchange channel may be used where the passive structures, orifices and/or mechanisms let down the pressure to the desired pressure. By controlling the temperature within each heat exchange channel, the temperature in the process microchannels can be controlled. Thus, for example, each process microchannel may be operated at a desired temperature by employing a specific pressure in the heat exchange channel adjacent to or in thermal contact with the process microchannel. This provides the advantage of precisely controlled temperatures for each process microchannel. The use of precisely controlled temperatures for each process microchannel provides the advantage of a tailored temperature profile and an overall reduction in the energy requirements for the process.

In a scale up device, for certain applications, it may be required that the mass of the process fluid be distributed uniformly among the process microchannels. Such an application may be when the process fluid is required to be cooled down with adjacent heat exchange channels. The uniform mass flow distribution may be obtained by changing the cross-sectional area from one parallel microchannel to another microchannel. The uniformity of mass flow distribution may be defined by Quality Index Factor (Q-factor) as indicated below. A Q-factor of 0% means absolute uniform distribution.

$$Q = \frac{\dot{m}_{max} - \dot{m}_{min}}{\dot{m}_{max}} \times 100$$

A change in the cross-sectional area may result in a difference in shear stress on the wall. In one embodiment, the Q-factor for the microchannel reactor 200 may be less than about 50%, and in one embodiment less than about 20%, and in one embodiment less than about 5%, and in one embodiment less than about 1%.

The superficial velocity for fluid flowing in the process microchannels may be at least about 0.01 meters per second (m/s), and in one embodiment at least about 0.1 m/s, and in one embodiment in the range from about 0.01 to about 100 m/s, and in one embodiment in the range from about 0.01 to about 1 m/s, and in one embodiment in the range from about 0.1 to about 10 m/s, and in one embodiment in the range from about 1 to about 100 m/s.

The free stream velocity for fluid flowing in the process microchannels may be at least about 0.001 m/s, and in one embodiment at least about 0.01 m/s, and in one embodiment in the range from about 0.001 to about 200 m/s, and in one embodiment in the range from about 0.01 to about 100 m/s, and in one embodiment in the range from about 0.01 to about 200 m/s.

The conversion of CO may be about 40% or higher per cycle, and in one embodiment about 50% or higher, and in one embodiment about 55% or higher, and in one embodiment about 60% or higher, and in one embodiment about 65% or higher, and in one embodiment about 70% or higher. The term "cycle" is used herein to refer to a single pass of the reactants through the process microchannels.

The yield of product may be about 25% or higher per cycle, and in one embodiment about 30% or higher, and in one embodiment about 40% or higher per cycle.

The nitrogen separator 300 may comprise a microchannel separator employing an ionic liquid as a liquid absorbent. The microchannel separator may comprise a thin film separator wherein the flow of the liquid absorbent (i.e., the ionic liquid) is retained or constrained within a channel or structure by the use of capillary forces that minimize the mixing or back mixing of a liquid and a gas (e.g., air) in a microchannel. The microchannel separator may comprise a device wherein a fluid mixture of the liquid absorbent and gas are co-fed either inside or outside of the microchannel device and flow in a co-flow arrangement. The fluid may flow into and out of surface features in the device. The microchannel separator may comprise a device wherein the gas and liquid absorbent flows in a co-flow arrangement and are mixed to create a high interfacial area by flowing past a series of obstructions in the form of a porous packed bed of rings, spheres, or other shapes. The microchannel separator may comprise a device wherein a thin contactor plate separates the phases to assist with countercurrent flow. The contactor plate may have sufficiently small apertures such that capillary pressure of the liquid retains the liquid on one side of the contactor plate and the gaseous stream on the other side of the contactor plate. The ionic liquid that may be used as the liquid absorbent may comprise one or more quaternary imidazolium salts, and/or one or more quaternary aromatic 5- or 6-membered-ring heterocyclic compounds such as imidazolium salts, pyridinium salts, and the like. These may include 1-butyl-3-methylimidazolium hexafluorophosphate, 1-octyl-3-methylimidazolium hexafluorophosphate, 1-butyl-3-methylimidazolium nitrate, 1-octyl-3-methylimidazolium tetrafluoroborate, 1-ethyl-3-methylimidazolium ethylsulfate, and/or N-butylpyridinium tetrafluoroborate. Ionic liquids that may be used are disclosed in U.S. Pat. Nos. 6,579,343 B2 and 6,623,659 B2, U.S. Patent Publication 2006/0251588 A1, and international publication WO 02/34863 A1, these patents and publications being incorporated herein by reference.

In one embodiment, temperature swing adsorption (TSA) or pressure swing adsorption (PSA) techniques may be used in the nitrogen separator 300. TSA and PSA processes employing microchannel technology that may be used for the foregoing separations are disclosed in U.S. Pat. Nos. 6,508,862 B1 and 6,652,627 B1, and U.S. Patent Publication US 2005/0045030 A1, which are incorporated herein by reference.

The ionic liquid separators, TSA separators and/or PSA separators discussed above may also be used in the line between the gasifier 110 and the microchannel reactor 200 to separate out contaminant gases and materials (e.g. $CO_2$, sulfur compounds such as $H_2S$, particulate solids, and the like) from the synthesis gas formed in the gasifier 110.

Microchannel devices employing layers of nanofibers or nano-composite films may be employed in the line between the gasifier 110 and the microchannel reactor 200 to separate out contaminant materials from the synthesis gas. Nanofibers and nano-composite films that may be used are disclosed in U.S. Pat. Nos. 6,326,326 B1; 6,531,224 B1; 6,733,835 B2; 6,753,038 B2; 6,846,554 B2; and 7,122,106 B2; which are incorporated herein by reference.

The presence of contaminants such as sulfur, halogen, selenium, phosphorus, arsenic, and the like, in the synthesis gas flowing out of the gasifier 110 may be undesirable. The foregoing contaminants may be removed from the synthesis gas or have their concentrations reduced prior to conducting the reaction in the microchannel reactor 200. Techniques for removing these contaminants are well known to those of skill in the art. For example, ZnO guardbeds may be used in the line between the gasifier 110 and the microchannel reactor 200 for removing sulfur impurities. The contaminant level in the synthesis gas may be reduced to a level of up to about 5% by volume, and in one embodiment up to about 1% by volume, and in one embodiment up to about 0.1% by volume, and in one embodiment up to about 0.05% by volume.

The pyrolysis process that is conducted in the pyrolysis reactor 400 may comprise heating the carbonaceous material in the absence of oxygen or any other reagent, except possibly steam. The pyrolysis process may comprise an anhydrous process. The pyrolysis process may comprise a fast or flash pyrolysis process wherein the carbonaceous material is heated at temperature in the range from about 350° C. to about 500° C. over a relatively short period of time of up to about 2 seconds, and in one embodiment in the range from about 0.5 to about 2 seconds. The pyrolysis process may be used to produce a liquid product which may be referred to as pyrolytic oil. The pyrolysis process may be conducted in an auger reactor, ablative reactor, rotating cone, fluidized bed or circulating fluidized bed.

The pyrolysis reaction that is conducted in an auger reactor involves the use of a feed of hot sand and carbonaceous material particles at one end of a screw. The screw mixes the sand and carbonaceous material and conveys it along as the pyrolysis process proceeds.

The ablative process involves projecting carbonaceous material particles at high speed against a hot metal surface. This can be achieved by using a metal surface spinning at high speed within a bed of carbonaceous material particles. As an alternative, the particles may be suspended in a carrier gas and introduced at high speed through a cyclone whose wall is heated.

The rotating cone process involves heating a mixture of sand and carbonaceous material particles and introducing the mixture into a rotating cone. Due to the rotation of the cone, the mixture of sand and carbonaceous material is transported across the cone surface by centrifugal force as the pyrolysis process proceeds.

With the fluidized bed reactor, carbonaceous material particles are introduced into a bed of hot sand fluidized by a gas. High heat transfer rates from the fluidized sand result in rapid heating of the carbonaceous material particles. Heat may be provided by heat exchanger tubes through which hot combustion gas may flow.

With the circulating fluidized beds, carbonaceous material particles are introduced into a circulating fluidized bed of hot sand. Gas, sand and carbonaceous material particles move together. The transport gas may be a recirculated product gas, although it may also be a combustion gas. High heat transfer rates from the sand provide for rapid heating of carbonaceous material particles. A separator may separate the product gases and vapors from the sand and char particles. The sand particles may be reheated in a fluidized burner vessel and recycled to the reactor.

The methanol produced in the microchannel reactor 200 may converted to one or more olefins. This reaction, which may be conducted in a microchannel reactor in the presence of a catalyst, may be represented, for example, by the equation:

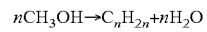

$$nCH_3OH \rightarrow C_nH_{2n} + nH_2O$$

where n is a number in the range from 2 to about 6, and in one embodiment n is 2 or 3. The reaction product may comprise $C_2$ and $C_3$ olefins with smaller amounts of $C_4$, $C_5$ and $C_6$ olefins. Aromatic compounds as well as higher olefin products may be formed. The higher olefins may include, for example, $C_8$ to $C_{30}$ olefins. The product mixture may depend on the catalyst and process conditions that are used. The catalyst may be a silico-alumino-phosphate catalyst of the type disclosed in U.S. Pat. No. 6,334,994 B2, which is incorporated herein by reference. This reaction may be highly exothermic and thus is particularly suitable for being conducted in a microchannel reactor where it is possible to provide enhanced temperature control. On the other hand, in conventional (i.e., non-microchannel) reactors, this reaction often tends to runaway resulting in possible coking and catalyst deactivation. When conducting this reaction in a microchannel reactor it may be possible to optimize single pass-through olefin yields at high throughputs while minimizing the formation of methane. The catalyst used with this reaction may be sensitive to hydrothermal deactivation. This catalyst may be regenerated while in the microchannel reactor using air oxidation or hydrogen in combination with methanol.

The methane produced in the microchannel reactor 200 may be converted to ethane or ethylene in a microchannel reactor in the presence of an oxidative coupling catalyst. This reaction may be conducted in the microchannel reactor 200 or downstream in a separate microchannel reactor. The reaction, which may be referred to as an oxidative complexing reaction, may be represented by the equation:

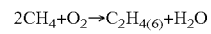

$$2CH_4 + O_2 \rightarrow C_2H_{4(6)} + H_2O$$

This reaction is exothermic and heat management for this reaction may be an important engineering consideration. Thus, this reaction is particularly suitable for being conducted in a microchannel reactor where it is possible to provide enhanced heat management control. The catalyst may comprise Li/MgO, $Rb_2WO_4$ or $Na_2WO_4$ on silica, $La_2O_3$—$CeO_2$ or BaO—$YsO_3$. This reaction is described in Holmen, "Direct Conversion of Methane to Fuels and Chemicals," Catalysis Today 142 (2009) 2-8, which is incorporated herein by reference.

The microchannel reactors used for the reaction of $CO_2$ with methane, the conversion of methanol to olefins, and for the oxidative coupling of methane, may each comprise a plurality of process microchannels and heat exchange channels stacked one above the other. These microchannel reactors may be in the form of cubic blocks as illustrated in FIGS. 8 and 9. Each cubic block may have a length in the range from about 10 to about 1000 cm, and in one embodiment in the range from about 20 to about 200 cm. The cubic block may have a width in the range from about 10 to about 1000 cm, and in one embodiment in the range from about 20 to about 200 cm. The cubic block may have a height in the range from about 10 to about 1000 cm, and in one embodiment in the range from about 20 to about 200 cm. The reactants may enter the process microchannels, and the product may flow out of the process microchannels. Heat exchange fluid may flow through the heat exchange channels. Each microchannel reactor may have a feed stream header or manifold to provide for the flow of the reactants into the process microchannels, a product footer or manifold to provide for the flow of product out of the process microchannels, a heat exchange inlet manifold to provide for the flow of heat exchange fluid into the heat exchange channels, and a heat exchange outlet manifold to provide for the flow of heat exchange fluid out of the heat exchange channels. Each microchannel reactor may contain one or more repeating units. Each repeating unit may contain one or more process microchannels and one or more heat exchange channels. Each of the process microchannels may contain one or more reaction zones wherein the reactants react in the presence of the catalyst to form the product. The catalyst may be present in the one or more reaction zones.

EXAMPLE

Figure 22:
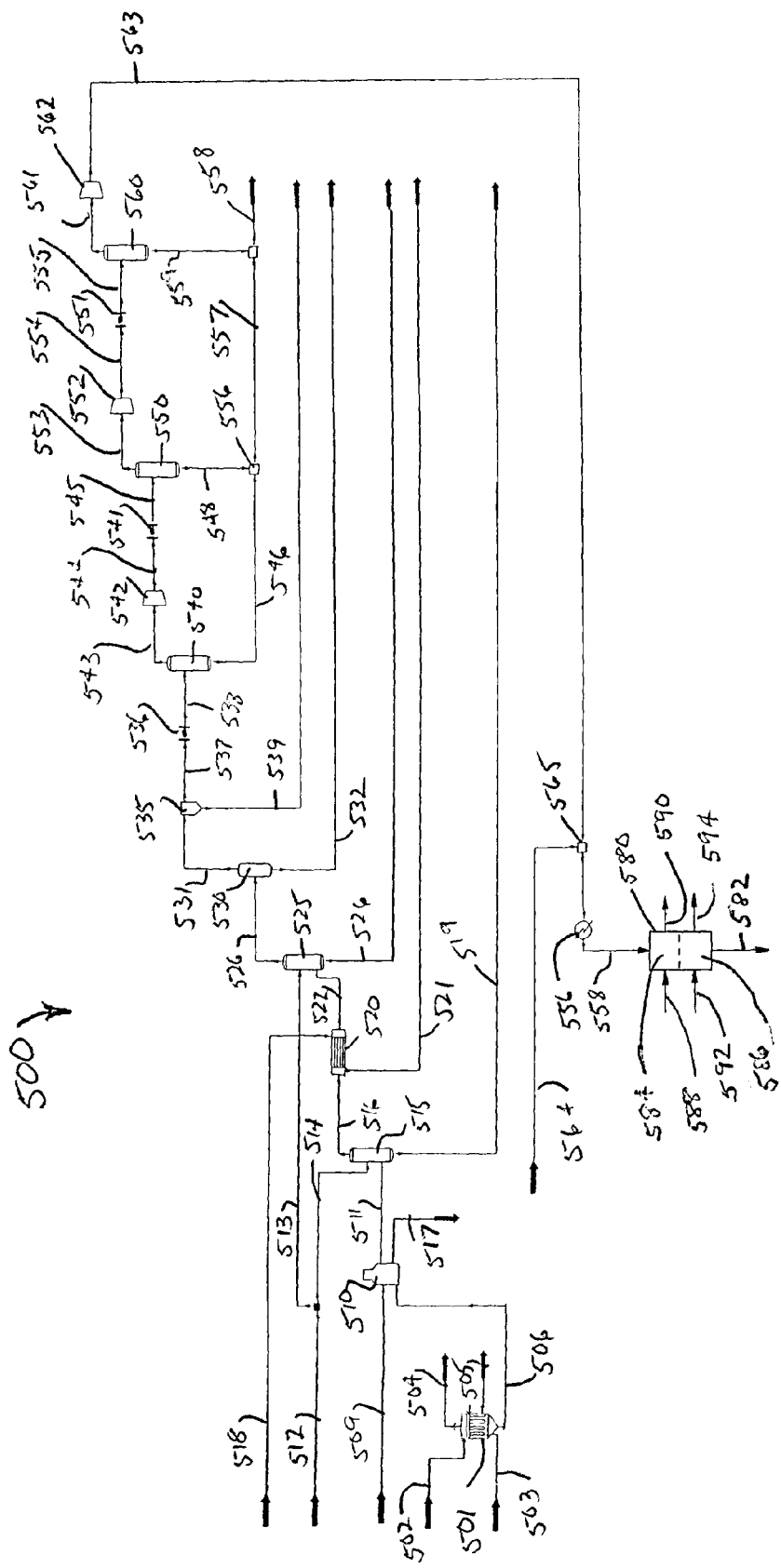
FIG. 22 is a flow sheet of the process disclosed in the Example.

A process for converting municipal solid waste (MSW) to dimethyl ether is disclosed in FIG. 22. Referring to FIG. 22, the process 500 involves the use of dryer 501, gasifier 510, tempering chamber 515, super heater 520, quench chamber 525, scrubber 530, cyclone 535, condensers 540, 550 and 560, mixer 565, and microchannel reactor 580. The process also employs the use of heat exchangers 536, 541, 551, and 556. These heat exchangers may be microchannel heat exchangers. Compressors 542, 552 and 562 are also employed in the illustrated process.

The operation of the process 500 illustrated in FIG. 22 will now be described. MSW with a water content of 70% by weight flows through line 502 into dryer 501 wherein the MSW undergoes condensation. Separated water flows out of the dryer 501 through line 504. Steam flows through line 503 into the dryer 501, heats the MSW, and flows out of the dryer 501 through line 505. Condensed MSW with a water concentration of 14.2% by weight flows through line 506 to gasifier 510. Oxygen flows through line 509 to gasifier 510. In gasifier 510, the MSW and the oxygen are heated and undergo a gasification reaction to form synthesis gas. Ash is removed from the gasifier 510 as indicated by arrow 517.

The synthesis gas flows from the gasifier 510 through line 511 to tempering chamber 515. Water flows through lines 512 and 514 to tempering chamber 515. Steam flows out of the tempering chamber 515 through line 519. The synthesis gas flows from tempering chamber 515 through line 516 to superheater 520. Steam flows through line 518 to and through superheater 520, and then out of superheater 520 through line 521. The synthesis gas flows from superheater 520 through line 522 to and through quenching chamber 525. Water flows through lines 512 and 513 to and through quenching chamber 525, and then out of quenching chamber 525 through line 526. The synthesis gas flows from the quenching chamber 525 through line 526 into scrubber 530. Contaminants are separated from the synthesis gas in the scrubber 530 and flow out of the scrubber through line 532. The synthesis gas flows from scrubber 530 through line 531 into cyclone 535. Solid particulates are separated from the synthesis gas in cyclone 535. The solid particulates are removed through line 539. The synthesis gas flows from cyclone 535 through line 537 to and through heat exchanger 536, and then through line 538 into condenser 540 where it is condensed. Water flows out of condenser 540 through line 546. The synthesis gas flows from condenser 540 through line 543 to and through compressor 542, and then from compressor 542 through line 544 to and through heat exchanger 541. The synthesis gas flows from heat exchanger 541 through line 545 to condenser 550 where it is condensed. Water is removed from the synthesis gas in condenser 550 and flows out of the condenser through line 548. The synthesis gas flows from condenser 550 through line 553 to and through compressor 552, and then from compressor 552 through line 554 to and through heat exchanger 551. The synthesis gas flows from heat exchanger 551 through line 555 to condenser 560 where it is condensed. Water flows out of the condenser 560 through line 559. The synthesis gas flows out of condenser 560 through line 561 to and through compressor 562.

The synthesis gas flows from compressor 562 through line 563 to mixer 565. The synthesis gas flowing through line 563 has a $H_2$:CO ratio of 1.0. Hydrogen flows through line 564 to mixer 565 wherein it is combined with the synthesis gas. The combined mixture of synthesis and hydrogen may be referred to as upgraded synthesis gas. The upgraded synthesis gas has a $H_2$:CO ratio of 2.6. The upgraded synthesis gas flows from mixer 565 through heat exchanger 556, and from the heat exchanger 556 through line 558 to microchannel reactor 580 wherein the synthesis gas undergoes an exothermic reaction to form a product comprising dimethyl ether.

The microchannel reactor 580 contains a plurality of process microchannels and a plurality of heat exchange channels. Each process microchannel contains reaction zones 584 and 586. The reaction zone 584 has a length of 2 cm, and the reaction zone 586 has a length of 8 cm. Each reaction zone contains a catalyst for converting synthesis gas to dimethyl ether. The reactions in each reaction zone are exothermic. The average temperature in the reaction zone 584 is 300° C. The average temperature in the reaction zone 586 is 225° C. Steam is used as a heat exchange fluid to control the temperature in each reaction zone. Steam flows through the heat exchange channels adjacent to the process microchannels containing the reaction zone 584 as indicated by arrows 588 and 590. Steam flows through the heat exchange channels adjacent to the process microchannels containing second reaction zone 586 as indicated by arrows 592 and 594. The synthesis gas enters the microchannel reactor 580 from line 558. The product comprising dimethyl ether flows out of the microchannel reactor 580 as indicated by arrow 582.

While the invention has been explained in relation to various embodiments, it is to be understood that various modifications thereof may become apparent to those skilled in the art upon reading this specification. Therefore, it is to be understood that the invention includes all such modifications that may fall within the scope of the appended claims.

The invention claimed is:

1. A process for converting a carbonaceous material to a desired product comprising methane, methanol or dimethyl ether, the carbonaceous material being selected from biomass and waste material, the process comprising:
   (A) gasifying the carbonaceous material in the presence of a gasification agent at a temperature of at least about 700° C. in a gasifier to form synthesis gas, the synthesis gas comprising $H_2$ and CO, water, particulate solids, and contaminants, the contaminants being selected from sulfur, halogen, selenium, phosphorus and arsenic; and flowing the synthesis gas out of the gasifier and reducing the temperature of the synthesis gas flowing out of the gasifier;

flowing the synthesis gas through one or more gas-liquid sorption devices, temperature swing adsorption devices, pressure swing adsorption devices, microchannel devices containing layers of nanofibers or nanocomposite films, cyclones and/or condensers to reduce the level of water, particulate solids and contaminants in the synthesis gas;

adding $H_2$ to the synthesis gas to form an upgraded synthesis gas with a molar ratio of $H_2$ to CO in the range from about 1.5 to about 4;

converting the upgraded synthesis gas to the desired product in a microchannel reactor, the microchannel reactor including a first reaction zone and another reaction zone and comprising a plurality of process microchannels and a plurality of heat exchange channels, the process microchannels having lengths in the range from about 0.2 to about 3 meters;

the upgraded synthesis gas being converted to the desired product using the following exothermic equilibrium limited reaction process steps (B)(I) and (B)(II); wherein step (B)(I) comprises flowing the upgraded synthesis gas through a first reaction zone in the microchannel reactor at a first reaction temperature in contact with a first catalyst to form an intermediate product composition, the first catalyst being in the form of a fixed bed of particulate solids, the particulate solids of the first catalyst having a median particle diameter in the range from about 1 to about 1000 microns, the intermediate product composition comprising $H_2$, CO and the desired product, the approach to equilibrium for conversion of the CO in the first reaction zone being at least about 5%; and step (B)(II) comprises flowing the intermediate product composition from the previous step through another reaction zone in the microchannel reactor at another reaction temperature in contact with another catalyst to form the desired product, the another catalyst being in the form of a fixed bed of particulate solids, the particulate solids of the another catalyst having a median particle diameter in the range from about 1 to about 1000 microns, the approach to equilibrium for conversion of the CO in the another reaction zone being at least about 5%, the another reaction temperature being at least about 5° C. less than the first reaction temperature; and flowing a heat exchange fluid in the heat exchange channels during steps (B)(I) and (B)(II), and transferring heat from the process microchannels to the heat exchange channels, wherein the heat exchange fluid used in the heat exchange channels during steps (B)(I) and (B)(II) comprises steam, liquid water and/or air, and at least part of the steam, liquid water and/or air used in the heat exchange channels during steps (B)(I) and (B)(II) flows from the heat exchange channels to the gasifier and is used as the gasification agent during step (A).

2. The process of claim 1 wherein nitrogen is separated from air in a nitrogen separator prior to step (A) to provide an oxygen enriched air or purified oxygen, and the carbonaceous material is gasified during step (A) in the presence of the oxygen enriched air or purified oxygen.

3. The process of claim 2 wherein the nitrogen is separated from the air in a microchannel separator using an ionic liquid as an absorbent liquid.

4. The process of claim 1 wherein the carbonaceous material is pyrolyzed prior to step (A) resulting in the formation of a pyrolytic oil, the pyrolytic oil being gasified during step (A).

5. The process of claim 1 wherein the level of sulfur contaminants in the synthesis gas is reduced using a ZnO guardbed.

6. The process of claim 1 wherein the carbonaceous material comprises municipal solid waste, hazardous waste, refuse derived fuel, tires, trash, sewage sludge, animal waste, petroleum coke, trash, garbage, agricultural waste, corn stover, switch grass, wood cuttings, timber, grass clippings, construction demolition materials, plastic material, cotton gin waste, or a mixture of two or more thereof.

7. The process of claim 1 wherein the ratio of $H_2$ to CO for the upgraded synthesis gas is in the range from about 1.5 to about 2.5.

8. The process of claim 1 wherein subsequent to step (B)(I) but prior to step (B)(II) the intermediate product composition formed in step (B)(I) flows through an additional reaction zone in the microchannel reactor at an additional reaction temperature in contact with an additional catalyst to form another intermediate product composition, the additional catalyst being in the form of a fixed bed of particulate solids, the particulate solids of the additional catalyst having a median particle diameter in the range from about 1 to about 1000 microns, the another intermediate product composition comprising synthesis gas and the desired product, the approach to equilibrium for the conversion of the synthesis gas in the additional reaction zone being at least about 5%.

9. The process of claim 1 wherein the conversion of CO in the first reaction zone is in the range from about 5% to about 95%, and the conversion of CO in the another reaction zone is in the range from about 5% to about 99%.

10. The process of claim 1 wherein the first catalyst in step (B)(I) has the same composition as the another catalyst in step (B)(II).

11. The process of claim 8 wherein the additional catalyst has the same composition as the first catalyst in step (B)(I), the another catalyst in step (B)(II), or both the first catalyst in step (B)(I) and the another catalyst in step (B)(II).

12. The process of claim 1 wherein the first catalyst in step (B)(I) has a different composition than the another catalyst in step (B)(II).

13. The process of claim 8 wherein the additional catalyst has a different composition than the first catalyst in step (B)(I), the another catalyst in step (B)(II), or both the first catalyst in step (B)(I) and the another catalyst in step (B)(II).

14. The process of claim 1 wherein the microchannel reactor comprises at least one manifold for flowing synthesis gas into the process microchannels, at least one manifold for flowing product out of the process microchannels, at least one manifold for flowing a heat exchange fluid into the heat exchange channels, and at least one manifold for flowing the heat exchange fluid out of the heat exchange channels.

15. The process of claim 1 wherein one or more microchannel reactors are used to form the desired product, the one or more microchannel reactors being positioned in a vessel.

16. The process of claim 15 wherein each microchannel reactor comprises from about 100 to about 50,000 process microchannels, and the vessel contains from 1 to about 1000 microchannel reactors.

17. The process of claim 15 wherein the vessel is a pressurized vessel.

18. The process of claim 1 wherein the process microchannels have an internal height of up to about 10 mm.

19. The process of claim 1 wherein the process microchannels and heat exchange channels are made of a material comprising: steel; aluminum; titanium; nickel; copper; an alloy of any of the foregoing metals; monel; inconel; brass; quartz; silicon; or a combination of two or more thereof.

20. The process of claim 1 wherein fluid flowing in the process microchannels contacts surface features in the process microchannels, the contacting of the surface features imparting a disruptive flow to the fluid.

21. The process of claim 1 wherein the heat exchange channels comprises microchannels.

22. The process of claim 1 wherein the process microchannels and the heat exchange channels have rectangular cross sections.

23. The process of claim 1 wherein the first catalyst and/or the another catalyst comprises a copper oxide, zinc oxide and/or an aluminum oxide.

24. The process of claim 23 wherein the first catalyst and/or the another catalyst further comprise an oxide of one or more rare earth elements, zirconium, yttrium, chromium, silver, gallium, vanadium, molybdenum, tungsten, titanium, or a mixture of two or more thereof.

25. The process of claim 1 wherein the first catalyst and/or the another catalyst comprise nickel, iron, cobalt, ruthenium, molybdenum, vanadium, titanium, an oxide of any of the foregoing metals, or a mixture of two or more of the foregoing metals and/or oxides.

26. The process of claim 1 wherein the first catalyst and/or another catalyst comprise vanadium and/or molybdenum in the form of a free metal, hydroxide, oxide and/or sulfide in combination with one or more salts, hydroxides, oxides or sulfides of one or more metals belonging to Group IA, IIA or IIIB from the Periodic Table.

27. The process of claim 1 wherein the process microchannels have at least one heat transfer wall, the heat flux for heat exchange within the microchannel reactor being in the range from about 0.01 to about 500 watts per square centimeter of surface area of the heat transfer wall.

28. The process of claim 1 wherein the pressure in the first reaction zone and/or the another reaction zone is in the range up to about 50 atmospheres.

29. The process of claim 1 wherein the average temperature in the first reaction zone is in the range from about 150 to about 400° C.

30. The process of claim 1 wherein the average temperature in the first reaction zone is in the range from about 250 to about 850° C.

31. The process of claim 1 wherein the contact time within the first reaction zone and/or the second reaction zone is up to about 2000 milliseconds.

32. The process of claim 1 wherein the process microchannels have fluid flowing in them in one direction, and the heat exchange channels have fluid flow in a direction that is co-current or counter-current to the flow of fluid in the process microchannels.

33. The process of claim 1 wherein the process microchannels have fluid flowing in them in one direction, and the heat exchange channels have fluid flowing in them in a direction that is cross-current to the flow of fluid in the process microchannels.

34. The process of claim 1 wherein the length of the process microchannels and the length of the heat exchange channels are about the same.

35. The process of claim 1 wherein the first catalyst and/or another catalyst comprise a graded catalyst.

36. The process of claim 1 wherein the Quality Index Factor for the microchannel reactor is less than about 50%.

37. The process of claim 1 wherein the superficial velocity for fluid flowing in the process microchannels is at least about 0.01 m/s.

38. The process of claim 1 wherein the space velocity for fluid flowing in the process microchannels is at least about 1000 hr$^{-1}$.

39. The process of claim 1 wherein the pressure drop for fluid flowing in the process microchannels is up to about 10 atmospheres per meter.

40. The process of claim 1 wherein the Reynolds number for the flow of fluid in the process microchannels is in the range from about 10 to about 4000.

41. The process of claim 1 wherein the process microchannels are formed by positioning a waveform between planar sheets.

42. The process of claim 1 wherein the heat exchange channels are formed by positioning a waveform between planar sheets.

43. The process of claim 1 wherein the desired product comprises methanol, and the methanol is converted to one or more olefins.

44. The process of claim 43 wherein the methanol is converted to one or more olefins in a microchannel reactor.

45. The process of claim 43 wherein the methanol is converted to one or more olefins in the presence of a silico-alumino-phosphate catalyst.

46. The process of claim 1 wherein the desired product comprises methane, and the methane is converted to ethane, ethylene, or a mixture thereof.

47. The process of claim 46 wherein the methane is converted to ethane, ethylene, or a mixture thereof, in a microchannel reactor.

48. The process of claim 46 wherein the methane is converted to ethane, ethylene, or a mixture thereof, in the presence of an oxidative coupling catalyst.

49. The process of claim 1 wherein the product comprises dimethyl ether and $CO_2$, the process further comprising reacting the $CO_2$ with methane to form a mixture of CO and $H_2$.

50. The process of claim 49 wherein the reaction of $CO_2$ with methane is conducted in a microchannel reactor.

51. The process of claim 1 wherein the microchannel reactor is constructed of stainless steel with one or more copper or aluminum waveforms being used for forming the process microchannels.

52. The process of claim 1 wherein at least part of the desired product is separated from the intermediate product composition subsequent to or during step (B)(I) but prior to step (B)(II).

53. The process of claim 1, wherein the carbonaceous material is gasified in a counter-current fixed bed gasifier to form the synthesis gas.

54. The process of claim 1, wherein the carbonaceous material is gasified in a co-current fixed bed gasifier to form the synthesis gas.

55. The process of claim 1, wherein the carbonaceous material is gasified in a plasma based gasification system to form the synthesis gas.

56. The process of claim 4, wherein liquid hydrocarbons are separated from the synthesis gas prior to step (B)(I) and are combined with the carbonaceous material prior to being pyrolyzed.

57. The process of claim 1, wherein the carbonaceous material is gasified in a fluidized bed gasifier.

58. The process of claim 1, wherein the carbonaceous material is gasified in an entrained flow gasifier.

59. The process of claim 1 wherein the particulate solids are separated from the synthesis gas by flowing the synthesis gas through a cyclone.

\* \* \* \* \*